(12) United States Patent
Chen et al.

(10) Patent No.: US 7,026,346 B2
(45) Date of Patent: Apr. 11, 2006

(54) COMPOUNDS AND METHODS FOR INDUCING APOPTOSIS IN PROLIFERATING CELLS

(75) Inventors: Ching-Shih Chen, Upper Arlington, OH (US); Xueqin Song, Ypsilanti, MI (US); Ho-Pi Lin, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 10/409,502

(22) Filed: Apr. 8, 2003

(65) Prior Publication Data

US 2003/0236294 A1   Dec. 25, 2003

Related U.S. Application Data

(60) Provisional application No. 60/370,664, filed on Apr. 8, 2002.

(51) Int. Cl.
*A61K 31/415* (2006.01)
*C07D 231/10* (2006.01)

(52) U.S. Cl. ............... 514/406; 548/356.1; 548/364.1; 548/373.1; 548/376.1

(58) Field of Classification Search ............ 548/356.1, 548/364.1, 373.1, 376.1; 514/406
See application file for complete search history.

(56) References Cited

U.S. PATENT DOCUMENTS

| | | | |
|---|---|---|---|
| 5,466,823 A | | 11/1995 | Talley et al. |
| 5,521,207 A | | 5/1996 | Graneto |
| 5,550,147 A | * | 8/1996 | Matsuo et al. ............... 514/406 |
| 5,760,068 A | | 6/1998 | Talley et al. |
| 5,972,986 A | | 10/1999 | Seibert et al. |
| 6,025,353 A | | 2/2000 | Masferrer et al. |

OTHER PUBLICATIONS

Groesch et al (2001): STN International CAPLUS database, Columbus (Ohio), Accession No.: 2001:912333.*
Johnson, et al.., "Apoptosis Signaling Pathways Mediated by Cyclooxygenase-2 Inhibitors in Prostate Cancer Cells," *Advan. Enzyme Regul.*, vol. 41, May 25, 2001, pp. 221-235.
Song, et al., "Cyclooxygenase-2, Player or Spectator in Cyclooxygenase-2 Inhibitor-Induced Apoptosis in Prostate Cancer Cells," *Journal of the National Cancer Inst.*, vol. 94, No. 8, Apr. 17, 2002, pp. 585-591.
Hsu, et al., "The Cyclooxygenase-2 Inhibitor Celecoxib Induces Apoptosis by Blocking Akt Activation in Human Prostate Cancer Cells Independently of Bcl-2," *The Journal of Biological Chemistry*, vol. 275, No. 15, Apr. 14, 2000, pp. 11397-11403.
Zhu, et al., "Using Cyclooxygenase-2 Inhibitors as Molecular Platforms to Develop a New Class of Apoptosis-Inducing Agents," *Journal of the National Cancer Inst.*, vol. 94, No. 23, Dec. 4, 2002, pp. 1745-1757.

* cited by examiner

*Primary Examiner*—Golam M. M. Shameem
(74) *Attorney, Agent, or Firm*—Calfee, Halter & Griswold, LLP

(57) ABSTRACT

Compounds useful for inducing apoptosis in proliferative cells, particularly cancer cells, including but not limited to prostate cancer, leukemia, non-smalll cell lung cancer, colon cancer, CNS cancer, melanoma, ovarian cancer, renal cancer, bladder cancer, lymphoma, and breast cancer. These compounds are particularly useful in the treatment of androgen-independent cancers, including hormone-refractory prostate cancer. Further provided are methods of treating cancer in a subject in need of such treatment using the compounds of the present invention. Further provided are methods for using the compounds of the present invention to treat, inhibit, or delay the onset of cancer in a subject. Further provided are methods of inducing apoptosis in rapidly proliferating cells, particularly, though not necessarily cancer cells, using the compounds of the present invention.

6 Claims, 12 Drawing Sheets

FIGURE 5

| R | Compd. | IC$_{50}$ (μM) COX-2 | T$_{1/2}$ (h) at 50 μM | R | Compd. | IC$_{50}$ (μM) COX-2 | T$_{1/2}$ (h) at 50 μM |
|---|---|---|---|---|---|---|---|
| ⟨⟩–CH₃ (p-CH) | cele-coxib | 0.04 | 2 | ⟨⟩–C₂H₅ | 4a | 0.86 | 2.5 |
| ⟨⟩–Cl | 1a | 0.01 | 2.5 | ⟨⟩–CF₃ | 5a | 8.23 | 2 |
| ⟨⟩–H | 2a | 0.032 | >100 | Cl-⟨⟩-Cl | 6a | >100 | 3 |
| ⟨⟩–NH | 3a | 0.34 | >100 | H₃C-⟨⟩-CH | 7a | >100 | 1 |

A

| Compound | Ar | $T_{1/2}$ (h) at 50 μM |
|---|---|---|
| 30b | 4-chlorophenyl | >24 |
| 31b | 2,4-dichlorophenyl | 3 |
| 32b | 2,5-dichlorophenyl | 3 |
| 33b | 3,4-dichlorophenyl | 3 |
| 34b | 4-methylphenyl | >24 |
| 35b | 4-(trifluoromethyl)-phenyl | >24 |
| 36b | 4-ethylphenyl | >24 |
| 37b | 2,4-dimethylphenyl | 2 |
| 38b | 2,5-dimethylphenyl | >24 |
| 39b | 3,5-dimethylphenyl | >24 |

B

C

A working model depicting the interaction between celecoxib and its protein target.

COMPOUNDS AND METHODS FOR INDUCING APOPTOSIS IN PROLIFERATING CELLS

CROSS-REFERENCE TO RELATED APPLICATION

This application claims priority to U.S. Provisional Patent Application 60/370,664, filed Apr. 8, 2002, the entirety of which is incorporated herein by reference.

STATEMENT REGARDING FEDERALLY SPONSORED RESEARCH OR DEVELOPMENT

This invention was made, at least in part, with government support under National Institutes of Health Grants CA92307 and CA94829 awarded by the National Cancer Institute, and under Army grant DAMD17-02-1-0117. The U.S. government may have certain rights in this invention.

BACKGROUND OF THE INVENTION

The present invention relates to agents and methods for treating cancer, particularly prostate cancer as well as other cancers, particularly androgen-insensitive cancers, in humans.

The mainstay of treatment for metastatic prostate cancer is hormonal or endocrine therapy (Kozlowski, J. M. et al. Urol. Clin. North Am. 18: 15–24 (1991), and Balmer, C. et al., Finley, R. S. and Balmer, C. (eds.), Concepts on Oncology Therapeutics, pp. 211–229, Bethesda: ASHP (1998)). It is aimed at androgen ablation by interfering either with androgen production or with the action of androgen within prostate cancer cells. Biochemical and morphological evidence has demonstrated that hormone ablation induces an active process that leads to apoptosis (programmed cell death) in androgen-sensitive prostate cancer cells (Kyprianou, N. Cancer Res. 50: 3748–53 (1990)). However, if a patient's prostate cancer progresses while receiving the first-line hormonal therapy, or if the patient never responds to the first-line hormonal his cancer is classified as androgen-insensitive or hormone-refractory prostate cancer (HRPC) (Kypianou, N. World J. Urol. 12: 299–303 (1994) and Bosland, M. C., Bertino, J. R. (ed.) Encyclopedia of Cancer, Vol. 2, pp. 1283–96, New York: Academic Press (1997)). Although the mechanism underlying the progression to an androgen-independent state remains elusive, it has been associated with the overexpression of the anti-apoptotic protein Bcl-2 or with abnormalities of the pro-apoptotic protein p53. Despite apoptosis resistance, androgen-independent prostate cancer cells still retain the basic machinery required for apoptosis. Nevertheless, HRPC always has a fatal outcome because the currently available chemotherapy regimens have limited impact on the survival of patients with HRPC (Kozlowski, J. M. et al. Urol. Clin. North Am. 18: 15–24 (1991), and Tannock, I. F. J. Clin. Oncol. 3: 1013–21 (1985)).

There remains a long-felt need for drugs that can induce apoptosis in patients with hormone refractory cancers such as HRPC. These drugs should work independent of androgen responsiveness, Bcl-2 levels, and p53 functional status. These drugs should have a high potency in inducing apoptosis in cancer cells while not adversely affecting normal cells. These drugs should further be well tolerated in humans and have few, if any, side effects.

SUMMARY OF THE INVENTION

Compounds useful for inducing apoptosis in proliferative cells, including but not limited to cancer cells, are given in formula I:

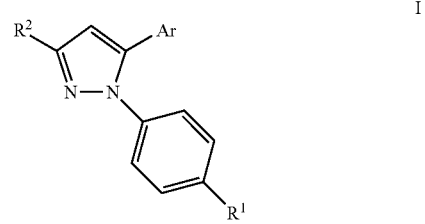

wherein $R^1$ is a group that is capable of forming hydrogen bonds, $R^2$ is a group that has a high electron density, and Ar is an aryl group. Preferably Ar has one or more substituents which provide hydrophobicity, because the substituents are non-polar, and/or steric effects, i.e. make the aryl group bulky. The hydrogen-bonding group $R^1$ is preferably an amide, more preferably a carboxyamide; $R^2$ is a group that has a high electron density, preferably an alkyl or haloalkyl group, more preferably trifluoromethyl; and Ar is selected from phenyl, biphenyl, naphthyl, anthryl, indolyl, pyrrolyl, and fluorenyl. Substituents on Ar include one or more radicals selected from the group consisting of halo, azido, $C_1$–$C_4$ alkyl, $C_1$–$C_4$ haloalkyl, $C_1$–$C_4$ azidoalkyl, aryl, alkylaryl, haloaryl, haloalkylaryl, and combinations thereof. Preferred groups for Ar include 2-naphthyl, 4-biphenyl, 9-anthryl, 2-fluorenyl, 4-azidophenyl, 4-azidomethylphenyl, 4-(2-azidoethyl)phenyl, 4-(3-azidopropyl)phenyl, 4-(4-azidobutyl)phenyl, 4-(4-azidophenyl)phenyl, 4-(4-azidomethylphenyl)phenyl, 4-methylphenyl, 4-ethylphenyl, 4-propylphenyl, 4-butylphenyl, 4-(2-bromoethyl)phenyl, 4-(3-bromopropyl)phenyl, 4-(4-bromobutyl)phenyl, 4-(trifluoromethyl)phenyl, 4-(4-methylphenyl)phenyl, 4-(4-bromomethylphenyl)phenyl, 4-(4-butylphenyl)phenyl, 4-(4-tert-butylphenyl)phenyl, 2-chlorophenyl, 4-chlorophenyl, 2,4-dichlorophenyl, 3,4-dichlorophenyl, 2,5-dichlorophenyl, 2,4-dimethylphenyl, 2,5-dimethylphenyl, 3,4-dimethylphenyl, 3,5-dimethylphenyl, 4-(4-chlorophenyl)phenyl, 4-(3,5-dichlorophenyl)phenyl, 4-(2,3-dichlorophenyl)phenyl, 4-(3,5-dimethylphenyl)phenyl, 4-(2,4,5-trichlorophenyl)phenyl, 4-(4-trifluoromethylphenyl)phenyl, 2-phenanthrenyl, 3-indolyl, 2-pyrrolyl, and 4-(benzyl)phenyl. The compounds of formula I are useful for treating, inhibiting, and delaying the onset of cancers, including, but not limited to leukemia, non-small cell lung cancer, colon cancer, CNS cancer, melanoma, ovarian cancer, renal cancer, prostate cancer, bladder cancer, lymphoma, and breast cancer, in mammals, especially in humans.

Further compounds of the present invention are those corresponding to formula II

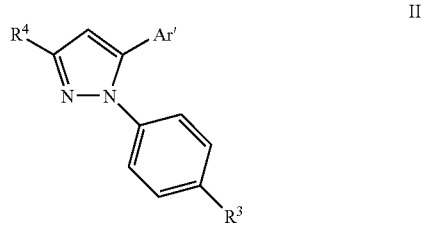

wherein R³ is a group capable of forming hydrogen-bonds. R³ is preferably an amide selected from carboxyamides and sulfonamides. R⁴ is selected from alkyl and haloalkyl; R⁴ is preferably trifluoromethyl. Ar' is a an aryl group that preferably has one or more substituents which provide hydrophobicity, because the substituents are non-polar, and/or steric effects, i.e. make the aryl group bulky. Preferred groups for Ar' include 4-azidophenyl, 4-(2-azidoethyl)phenyl, 4-(3-azidopropyl)phenyl, 4-(4-azidobutyl)phenyl, 4-(4-azidophenyl)phenyl, 4-(4-azidomethylphenyl)phenyl, 2,5-dimethylphenyl, 4-propylphenyl, 4-bromomethylphenyl, 4-(2-bromoethyl)phenyl, 4-(3-bromopropyl)phenyl, 4-(4-bromobutyl)phenyl, 4-(4-bromomethylphenyl)phenyl, 4-(4-tert-butylphenyl)phenyl, 9-anthryl, 4-(4-butylphenyl)phenyl, 4-(4-methylphenyl)phenyl, 4-(4-chlorophenyl)phenyl, 4-(3,5-dichlorophenyl)phenyl, 4-(2,3-dichlorophenyl)phenyl, 4-(3,5-dimethylphenyl)phenyl, 4-(2,4,5-trichlorophenyl)phenyl, 4-(4-trifluoromethylphenyl)phenyl, 2-phenanthrenyl, 3-indolyl, 2-pyrrolyl, 4-(benzyl)phenyl, and 2-fluorenyl.

Preferred compounds of formula II include:
4-[5-(4-azidophenyl)-3-(trifluoromethyl)-1H-pyrazol-1-yl]benzenesulfonamide;
4-[5-(4-(2-azidoethyl)phenyl)-3-(trifluoromethyl)-1-H-pyrazol-1-yl]benzenesulfonamide;
4-[5-(4-(3-azidopropyl)phenyl)-3-(trifluoromethyl)-1H-pyrazol-1-yl]benzenesulfonamide;
4-[5-(4-(4-methylphenyl)phenyl)-3-(trifluoromethyl)-1-H-pyrazol-1-yl]benzenesulfonamide;
4-[5-(4-(4-butylphenyl)phenyl)-3-(trifluoromethyl)-1H-pyrazol-1-yl]benzenesulfonamide;
4-[5-(4-(4-azidobutyl)phenyl)-3-(trifluoromethyl)-1H-pyrazol-1-yl]benzenesulfonamide;
4-[5-(4-(4-azidophenyl)phenyl)-3-(trifluoromethyl)-1H-pyrazol-1-yl]benzenesulfonamide;
4-[5-(4-(4-azidomethylphenyl)phenyl)-3-(trifluoromethyl)-1H-pyrazol-1-yl]benzenesulfonamide;
4-[5-(4-(4-chlorophenyl)phenyl)-3-(trifluoromethyl)-1H-pyrazol-1-yl]benzenesulfonamide;
4-[5-(4-(3,5-dichlorophenyl)phenyl)-3-(trifluoromethyl)-1H-pyrazol-1-yl]benzenesulfonamide;
4-[5-(4-(2,3-dichlorophenyl)phenyl)-3-(trifluoromethyl)-1H-pyrazol-1-yl]benzenesulfonamide;
4-[5-(4-(3,5-dimethylphenyl)phenyl)-3-(trifluoromethyl)-1H-pyrazol-1-yl]benzenesulfonamide;
4-[5-(4-(2,4,5-trichlorophenyl)phenyl)-3-(trifluoromethyl)-1H-pyrazol-1-yl]benzenesulfonamide;
4-[5-(4-(4-trifluoromethylphenyl)phenyl)-3-(trifluoromethyl)-1H-pyrazol-1-yl]benzenesulfonamid
4-[5-(2-phenanthrenyl)-3-(trifluoromethyl)-1H-pyrazol-1-yl]benzenesulfonamide;
4-[5-(3-indolyl)-3-(trifluoromethyl)-1H-pyrazol-1-yl]benzenesulfonamide;
4-[5-(2-pyrrolyl)-3-(trifluoromethyl)-1H-pyrazol-1-yl]benzenesulfonamide;
4-[5-(4-benzylphenyl)-3-(trifluoromethyl)-1H-pyrazol-1-yl]benzenesulfonamide;
4-[5-(4-azidophenyl)-3-(trifluoromethyl)-1H-pyrazol-1-yl]benzenecarboxyamide;
4-[5-(4-(2-azidoethyl)phenyl)-3-(trifluoromethyl)-1H-pyrazol-1-yl]benzenecarboxyamide;
4-[5-(4-(3-azidopropyl)phenyl)-3-(trifluoromethyl)-1H-pyrazol-1-yl]benzenecarboxyamide;
4-[5-(4-(4-azidobutyl)phenyl)-3-(trifluoromethyl)-1H-pyrazol-1-yl]benzenecarboxyamide;
4-[5-(4-(4-azidophenyl)phenyl)-3-(trifluoromethyl)-1H-pyrazol-1-yl]benzenecarboxyamide;
4-[5-(4-(4-azidomethylphenyl)phenyl)-3-(trifluoromethyl)-1H-pyrazol-1-yl]benzenecarboxyamide;
4-[5-(2,5-dimethylphenyl)-3-(trifluoromethyl)-1H-pyrazol-1-yl]benzenecarboxyamide;
4-[5-(4-propylphenyl)-3-(trifluoromethyl)-1H-pyrazol-1-yl]benzenecarboxyamide;
4-[5-(4-bromomethylphenyl)-3-(trifluoromethyl)-1H-pyrazol-1-yl]benzenecarboxyamide;
4-[5-(4-(2-bromoethyl)phenyl)-3-(trifluoromethyl)-1H-pyrazol-1-yl]benzenecarboxyamide;
4-[5-(4-(3-bromopropyl)phenyl)-3-(trifluoromethyl)-1H-pyrazol-1-yl]benzenecarboxyamide;
4-[5-(4-(4-bromobutyl)phenyl)-3-(trifluoromethyl)-1H-pyrazol-1-yl]benzenecarboxyamide;
4-[5-(4-(4-bromomethylphenyl)phenyl)-3-(trifluoromethyl)-1H-pyrazol-1-yl]benzenecarboxyamide;
4-[5-(4-(4-tert-butylphenyl)phenyl)-3-(trifluoromethyl)-1H-pyrazol-1-yl]benzenecarboxyamide;
4-[5-(9-anthryl)-3-(trifluoromethyl)-1H-pyrazol-1-yl]benzenecarboxyamide;
4-[5-(2-fluorenyl)-3-(trifluoromethyl)-1H-pyrazol-1-yl]benzenecarboxyamide 4-[5-(4-(4-methylphenyl)phenyl)-3-(trifluoromethyl)-1H-pyrazol-1-yl]benzenecarboxyamide;
4-[5-(4-(4-butylphenyl)phenyl)-3-(trifluoromethyl)-1H-pyrazol-1-yl]benzenecarboxyamide
4-[5-(4-(4-chlorophenyl)phenyl)-3-(trifluoromethyl)-1H-pyrazol-1-yl]benzenecarboxyamide;
4-[5-(4-(3,5-dichlorophenyl)phenyl)-3-(trifluoromethyl)-1H-pyrazol-1-yl]benzenecarboxyamide;
4-[5-(4-(2,3-dichlorophenyl)phenyl)-3-(trifluoromethyl)-1H-pyrazol-1-yl]benzenecarboxyamide;
4-[5-(4-(3,5-dimethylphenyl)phenyl)-3-(trifluoromethyl)-1H-pyrazol-1-yl]benzenecarboxyamide;
4-[5-(4-(2,4,5-trichlorophenyl)phenyl)-3-(trifluoromethyl)-1H-pyrazol-1-yl]benzenecarboxyamide;
4-[5-(4-(4-trifluoromethylphenyl)phenyl)-3-(trifluoromethyl)-1H-pyrazol-1-yl]benzenecarboxyamide;
4-[5-(2-phenanthrenyl)-3-(trifluoromethyl)-1H-pyrazol-1-yl]benzenecarboxyamide;
4-[5-(3-indolyl)-3-(trifluoromethyl)-1H-pyrazol-1-yl]benzenecarboxyamide;
4-[5-(2-pyrrolyl)-3-(trifluoromethyl)-1H-pyrazol-1-yl]benzenecarboxyamide; and
4-[5-(4-benzylphenyl)-3-(trifluoromethyl)-1H-pyrazol-1-yl]benzenecarboxyamide. 4-[5-(2-phenanthrenyl)-3-(trifluoromethyl)-1H-pyrazol-1-yl]benzenesulfonamide is an especially preferred compound of formula II.

The compounds of formulae I and II are useful in inducing apoptosis in proliferative cells, including, but not limited to cancer cells. The compounds are further useful for treating, inhibiting, and delaying the onset of cancer in mammals, and especially in humans. Cancers that these compounds work particularly well against include, but are not limited to, leukemia, non-small cell lung cancer, colon cancer, CNS cancer, melanoma, ovarian cancer, renal cancer, prostate cancer, bladder cancer, lymphoma, and breast cancer. Surprisingly, the compounds of the present invention are able to induce apoptosis in cancer cells independent of the level of Bcl-2 expression and p53 functional status, which means that the inventive compounds are potent even against cancers that are androgen-independent, such as hormone-refractory prostate cancer.

Accordingly, the present invention relates to compounds useful for inducing apoptosis in unwanted proliferative cells, including cancer cells. The present invention also relates to methods of using the inventive compounds to treat, to prevent, or to delay the onset of disorders characterized by unwanted, rapid cell proliferation, including but not limited to cancer. The present invention also relates methods of using the inventive compounds to treat specific kinds of cancers, including but not limited to leukemia, non-small cell lung cancer, colon cancer, CNS cancer, melanoma, ovarian cancer, renal cancer, prostate cancer, bladder cancer, lymphoma, and breast cancer. It further relates to methods of treating, preventing, and delaying the onset of androgen-independent cancers. It still further relates to methods of treating advanced prostate cancer.

BRIEF DESCRIPTION OF THE FIGURES

FIG. 5 shows the structure and characteristics of celecoxib and compounds 1a–7a.

DETAILED DESCRIPTION OF THE INVENTION

Figure 1:
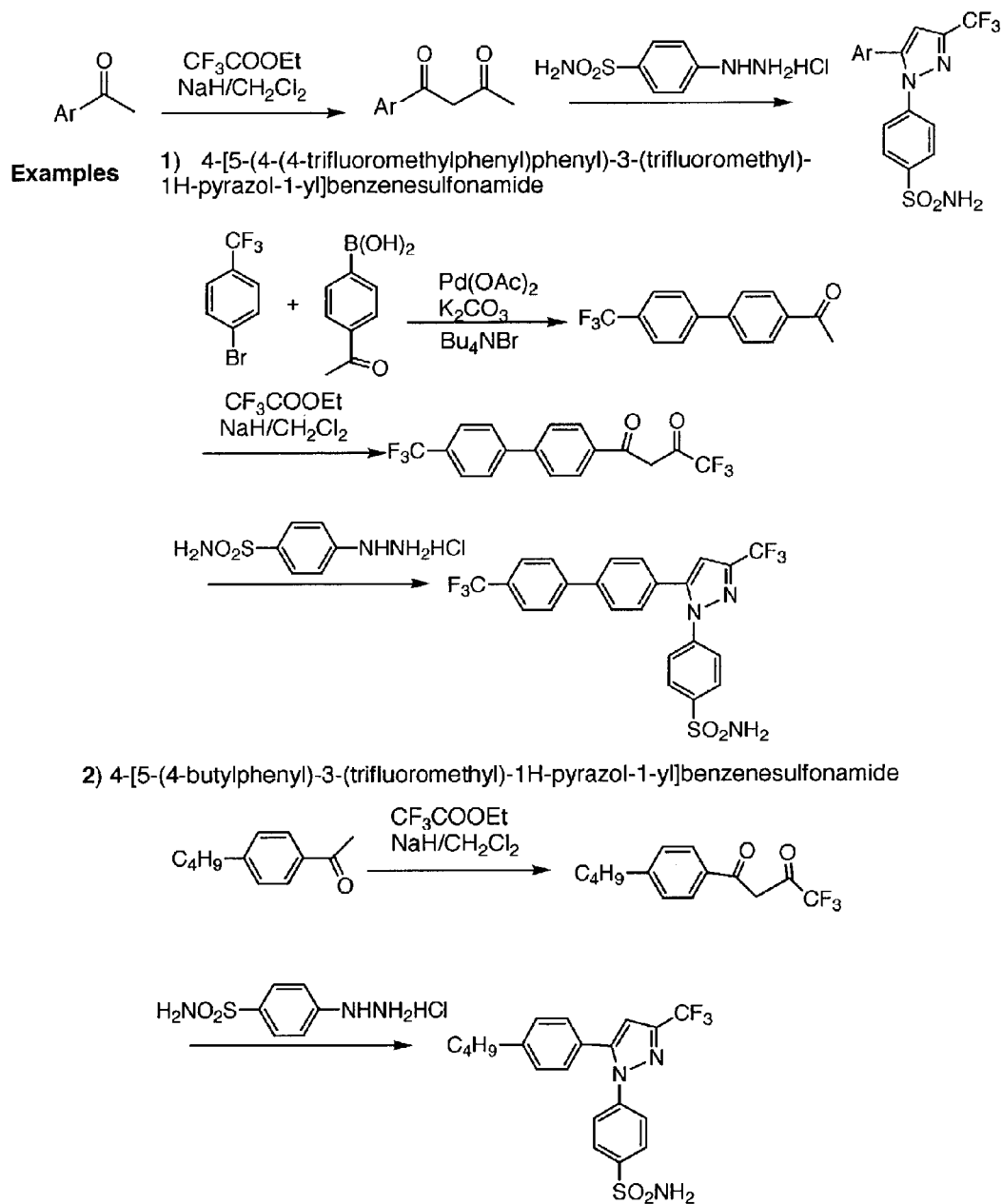
FIG. 1 shows a general synthetic scheme for preparing the compounds of the present invention.

The present invention provides compounds useful for inducing apoptosis in undesirable proliferating cells as well as methods of using these compounds to induce apoptosis in the undesirable proliferating cells in subjects in need of such treatment. The method involves treating the subject in need of such treatment with a therapeutically effective amount of a compound of the present invention or a derivative or pharmaceutically acceptable salt thereof.

The compounds and methods of the present invention are useful for, but not limited to treating, inhibiting, or delaying the onset of cancers. The compounds and methods are also useful in the treatment of precancers and other incidents of undesirable cell proliferation. According to the present invention, the compounds of formula I or II are administered to a subject experiencing undesirable cell proliferation. The compounds and methods are useful for treating cancers including, but not limited to, leukemia, non-small cell lung cancer, colon cancer, CNS cancer, melanoma, ovarian cancer, renal cancer, prostate cancer, bladder cancer, lymphoma, and breast cancer. Furthermore, they are useful in the prevention of these cancers in individuals with precancers, as well as individuals prone to these disorders.

The term "treatment" includes partial or total destruction of the undesirable proliferating cells with minimal destructive effects on normal cells. In accordance with the present invention, a desired mechanism of treatment at the cellular level is apoptosis.

The term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject who has a disorder characterized by unwanted, rapid cell proliferation. Such disorders include, but are not limited to cancers and precancers. For methods of prevention the subject is any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

The compounds of the present invention may trigger cell death by a number of different mechanisms, however, an aspect of the inventive compounds is that they are able to induce apoptosis in unwanted, proliferative cells. The term "apoptosis" refers to the process of programmed cell death. In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self destruct. Apoptosis is distinguished from other mechanisms of cell death, such as necrosis, which results in inflammation including swelling, redness, pain and tenderness. Apoptosis does not stimulate such reactions. In apoptosis, the cells shrivel up, break into pieces and the contents are quietly removed by methods that do not induce inflammation. For these reasons, it is highly desirable to induce apoptosis, rather than necrosis, in rapidly proliferating cells, such as cancer cells. However, mutations in some cancer cells confer resistance of these cells to apoptosis. The compounds of formulae I and II have been found to induce apoptosis even in cancer cells which, because of mutations, are otherwise resistant to apoptosis. Apoptosis can be distinguished from other treatment mechanisms by methods such as microscopy, which are known in the art.

The terms "proliferative cells," "proliferating cells," "rapidly proliferating cells," "undesirable proliferating cells," "undesirable rapidly proliferating cells," "unwanted rapidly proliferating cells," and the like, refer to cancer cells, precancer cells, and other abnormal, rapidly dividing cells in a subject.

The term "COX-2 inhibitory" as used herein refers to compounds that can effectively inhibit the cyclooxygenase-2 (COX-2) enzyme, and is generally expressed as an $IC_{50}$ value (concentration for 50% inhibition). Unfortunately, COX-2 inhibitors have been found to have potentially severe gastrointestinal toxicity, including upper GI ulcers, gross bleeding, ulceration, and perforation of the stomach, small intestine, or large intestine, sometimes resulting in death. These risks are greatly increased for patients with a prior history of peptic ulcer disease and/or gastrointestinal bleeding, as well as those patients who take certain medications such as anticoagulants, or smoke, and for those patients who are older or in poor general health. Furthermore, these risks increase as treatment progresses. Because of these risks, it is desirable that the compounds of the present invention are not COX-2 inhibitory. Accordingly, it is highly desirable that the compounds of the present invention have an $IC_{50}$ of 100 μM or more with respect to COX-2.

The compounds of the present invention are represented in formula I:

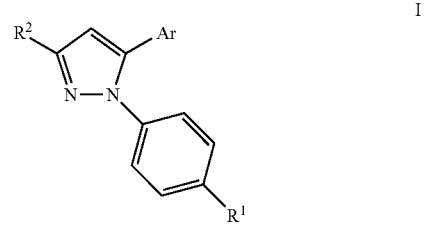

wherein $R^1$ is a group that is capable of forming hydrogen bonds, $R^2$ is a group that preferably has a high electron density, and Ar is an aryl group that is preferably bulky. The hydrogen-bonding group $R^1$ is preferably an amide, and most preferably a carboxyamide. $R^2$ is preferably an alkyl or haloalkyl radical, more preferably, $R^2$ is a $C_1$–$C_4$ haloalkyl, and even more preferably, $R^2$ is trifluoromethyl. Ar is an aryl radical selected from phenyl, biphenyl, naphthyl, anthryl, and fluorenyl; and Ar is preferably substituted at one or more substitutable positions with one or more radicals selected from halo, azido, $C_1$–$C_4$ alkyl, $C_1$–$C_4$ haloalkyl, $C_1$–$C_4$ azidoalkyl, aryl, alkylaryl, haloaryl, haloalkylaryl, and combinations thereof.

A preferred class of compounds of the present invention are those of formula I wherein $R^1$ is carboxyamide, $R^2$ is trifluoromethyl, and Ar is selected from 2-naphthyl, 4-biphenyl, 9-anthryl, 2-fluorenyl, 4-azidophenyl, 4-azidomethylphenyl, 4-(2-azidoethyl)phenyl, 4-(3-azidopropyl)phenyl, 4-(4-azidobutyl)phenyl, 4-(4-azidophenyl)phenyl, 4-(4-azidomethylphenyl)phenyl, 4-methylphenyl, 4-ethylphenyl, 4-propylphenyl, 4-butylphenyl, 4-(2-bromoethyl)phenyl, 4-(3-bromopropyl)phenyl, 4-(4-bromobutyl)phenyl, 4-(trifluoromethyl)phenyl, 4-(4-methylphenyl)phenyl, 4-(4-bromomethylphenyl)phenyl, 4-(4-butylphenyl)phenyl, 4-(4-tert-butylphenyl)phenyl, 2-chlorophenyl, 4-chlorophenyl, 2,4-dichlorophenyl, 3,4-dichlorophenyl, 2,5-dichlorophenyl, 2,4-dimethylphenyl, 2,5-dimethylphenyl, 3,4-dimethylphenyl, 3,5-dimethylphenyl, 4-(4-chlorophenyl)phenyl, 4-(3,5-dichlorophenyl)phenyl, 4-(2,3-dichlorophenyl)phenyl, 4-(3,5-dimethylphenyl)phenyl, 4-(2,4,5-trichlorophenyl)phenyl, 4-(4-trifluoromethylphenyl)phenyl, 2-phenanthrenyl, 3-indolyl, 2-pyrrolyl, and 4-(benzyl)phenyl. Those of skill in the art will recognize other substituted aryl radicals that could also be used.

A family of specific compounds of formula I consists of the following compounds and pharmaceutically acceptable salts thereof:

4-[5-(2-naphthyl)-3-(trifluoromethyl)-1H-pyrazol-1-yl]benzenecarboxyamide;

4-[5-(4-biphenyl)-3-(trifluoromethyl)-1H-pyrazol-1-yl]benzenecarboxyamide;

4-[5-(9-anthryl)-3-(trifluoromethyl)-1H-pyrazol-1-yl]benzenecarboxyamide;

4-[5-(2-fluorenyl)-3-(trifluoromethyl)-1H-pyrazol-1-yl]benzenecarboxyamide;

4-[5-(4-azidophenyl)-3-(trifluoromethyl)-1H-pyrazol-1-yl]benzenecarboxyamide;

4-[5-(4-azidomethylphenyl)-3-(trifluoromethyl)-1H-pyrazol-1-yl]benzenecarboxyamide;

4-[5-(4-(2-azidoethyl)phenyl)-3-(trifluoromethyl)-1H-pyrazol-1-yl]benzenecarboxyamide;

4-[5-(4-(3-azidopropyl)phenyl)-3-(trifluoromethyl)-1H-pyrazol-1-yl]benzenecarboxyamide;
4-[5-(4-(4-azidobutyl)phenyl)-3-(trifluoromethyl)-1H-pyrazol-1-yl]benzenecarboxyamide;
4-[5-(4-(4-azidophenyl)phenyl)-3-(trifluoromethyl)-1H-pyrazol-1-yl]benzenecarboxyamide;
4-[5-(4-(4-azidomethylphenyl)phenyl)-3-(trifluoromethyl)-1H-pyrazol-1-yl]benzenecarboxyamide;
4-[5-(4-methylphenyl)-3-(trifluoromethyl)-1H-pyrazol-1-yl]benzenecarboxyamide;
4-[5-(4-ethylphenyl)-3-(trifluoromethyl)-1H-pyrazol-1-yl]benzenecarboxyamide;
4-[5-(4-propylphenyl)-3-(trifluoromethyl)-1H-pyrazol-1-yl]benzenecarboxyamide;
4-[5-(4-butylphenyl)-3-(trifluoromethyl)-1H-pyrazol-1-yl]benzenecarboxyamide;
4-[5-(4-(2-bromoethyl)phenyl)-3-(trifluoromethyl)-1H-pyrazol-1-yl]benzenecarboxyamide;
4-[5-(4-(3-bromopropyl)phenyl)-3-(trifluoromethyl)-1H-pyrazol-1-yl]benzenecarboxyamide;
4-[5-(4-(4-bromobutyl)phenyl)-3-(trifluoromethyl)-1H-pyrazol-1-yl]benzenecarboxyamide;
4-[5-(4-(trifluoromethyl)phenyl)-3-(trifluoromethyl)-1H-pyrazol-1-yl]benzenecarboxyamide;
4-[5-(4-(4-methylphenyl)phenyl)-3-(trifluoromethyl)-1H-pyrazol-1-yl]benzenecarboxyamide;
4-[5-(4-(4-bromomethylphenyl)phenyl)-3-(trifluoromethyl)-1H-pyrazol-1-yl]benzenecarboxyamide;
4-[5-(4-(4-butylphenyl)phenyl)-3-(trifluoromethyl)-1H-pyrazol-1-yl]benzenecarboxyamide;
4-[5-(4-(4-tert-butylphenyl)phenyl)-3-(trifluoromethyl)-1H-pyrazol-1-yl]benzenecarboxyamide;
4-[5-(2-chlorophenyl)-3-(trifluoromethyl)-1H-pyrazol-1-yl]benzenecarboxyamide;
4-[5-(4-chlorophenyl)-3-(trifluoromethyl)-1H-pyrazol-1-yl]benzenecarboxyamide;
4-[5-(2,4-dichlorophenyl)-3-(trifluoromethyl)-1H-pyrazol-1-yl]benzenecarboxyamide;
4-[5-(3,4-dichlorophenyl)-3-(trifluoromethyl)-1H-pyrazol-1-yl]benzenecarboxyamide;
4-[5-(2,5-dichlorophenyl)-3-(trifluoromethyl)-1H-pyrazol-1-yl]benzenecarboxyamide;
4-[5-(2,4-dimethylphenyl)-3-(trifluoromethyl)-1H-pyrazol-1-yl]benzenecarboxyamide;
4-[5-(2,5-dimethylphenyl)-3-(trifluoromethyl)-1H-pyrazol-1-yl]benzenecarboxyamide;
4-[5-(3,4-dimethylphenyl)-3-(trifluoromethyl)-1H-pyrazol-1-yl]benzenecarboxyamide;
4-[5-(3,5-dimethylphenyl)-3-(trifluoromethyl)-1H-pyrazol-1-yl]benzenecarboxyamide;
4-[5-(4-(4-chlorophenyl)phenyl)-3-(trifluoromethyl)-1H-pyrazol-1-yl]benzenecarboxyamide;
4-[5-(4-(3,5-dichlorophenyl)phenyl)-3-(trifluoromethyl)-1H-pyrazol-1-yl]benzenecarboxyamide;
4-[5-(4-(2,3-dichlorophenyl)phenyl)-3-(trifluoromethyl)-1H-pyrazol-1-yl]benzenecarboxyamide;
4-[5-(4-(3,5-dimethylphenyl)phenyl)-3-(trifluoromethyl)-1H-pyrazol-1-yl]benzenecarboxyamide;
4-[5-(4-(2,4,5-trichlorophenyl)phenyl)-3-(trifluoromethyl)-1H-pyrazol-1-yl]benzenecarboxyamide;
4-[5-(4-(4-trifluoromethylphenyl)phenyl)-3-(trifluoromethyl)-1H-pyrazol-1-yl]benzenecarboxyamide;
4-[5-(2-phenanthrenyl)-3-(trifluoromethyl)-1H-pyrazol-1-yl]benzenecarboxyamide;
4-[5-(3-indolyl)-3-(trifluoromethyl)-1H-pyrazol-1-yl]benzenecarboxyamide;
4-[5-(2-pyrrolyl)-3-(trifluoromethyl)-1H-pyrazol-1-yl]benzenecarboxyamide; and
4-[5-(4-(benzyl)phenyl)-3-(trifluoromethyl)-1H-pyrazol-1-yl]benzenecarboxyamide.

A second class of compounds of the present invention are those of formula II:

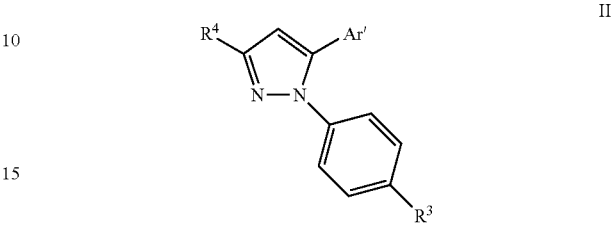

wherein $R^3$ is a group that is capable of forming hydrogen bonds, $R^4$ is a group that preferably has a high electron density, and Ar is an aryl group that is preferably bulky. $R^3$ is preferably an amide selected from carboxyamide and sulfonamide. $R^4$ is selected from alkyl and haloalkyl, and is preferably $C_1$–$C_4$ alkyl or $C_1$–$C_4$ haloalkyl, and is even more preferably trifluoromethyl. Ar' is selected from 4-azidophenyl, 4-(2-azidoethyl)phenyl, 4-(3-azidopropyl)phenyl, 4-(4-azidobutyl)phenyl, 4-(4-azidophenyl)phenyl, 4-(4-azidomethylphenyl)phenyl, 2,5-dimethylphenyl, 4-propylphenyl, 4-bromomethylphenyl, 4-(2-bromoethyl)phenyl, 4-(3-bromopropyl)phenyl, 4-(4-bromobutyl)phenyl, 4-(4-bromomethylphenyl)phenyl, 4-(4-tert-butylphenyl)phenyl, 9-anthryl, 4-(4-butylphenyl)phenyl, 4-(4-methylphenyl)phenyl, 4-chlorophenyl, 4-(3,5-dichlorophenyl)phenyl, 4-(2,3-dichlorophenyl)phenyl, 4-(3,5-dimethylphenyl)phenyl, 4-(2,4,5-trichlorophenyl)phenyl, 4-(4-trifluoromethylphenyl)phenyl, 2-phenanthrenyl, 3-indolyl, 2-pyrrolyl, 4-(benzyl)phenyl, and 2-fluorenyl.

A family of specific compounds of particular interest within formula II consists of the following compounds and derivatives and pharmaceutically acceptable salts thereof:
4-[5-(4-azidophenyl)-3-(trifluoromethyl)-1H-pyrazol-1-yl]benzenesulfonamide;
4-[5-(4-(2-azidoethyl)phenyl)-3-(trifluoromethyl)-1H-pyrazol-1-yl]benzenesulfonamide;
4-[5-(4-(3-azidopropyl)phenyl)-3-(trifluoromethyl)-1H-pyrazol-1-yl]benzenesulfonamide;
4-[5-(4-(4-azidobutyl)phenyl)-3-(trifluoromethyl)-1H-pyrazol-1-yl]benzenesulfonamide;
4-[5-(4-(4-butylphenyl)phenyl)-3-(trifluoromethyl)-1H-pyrazol-1-yl]benzenesulfonamide;
4-[5-(4-(4-methylphenyl)phenyl)-3-(trifluoromethyl)-1H-pyrazol-1-yl]benzenesulfonamide;
4-[5-(4-(4-azidophenyl)phenyl)-3-(trifluoromethyl)-1H-pyrazol-1-yl]benzenesulfonamide;
4-[5-(4-(4-azidomethylphenyl)phenyl)-3-(trifluoromethyl)-1H-pyrazol-1-yl]benzenesulfonamide;
4-[5-(4-(4-chlorophenyl)phenyl)-3-(trifluoromethyl)-1H-pyrazol-1-yl]benzenesulfonamide;
4-[5-(4-(3,5-dichlorophenyl)phenyl)-3-(trifluoromethyl)-1H-pyrazol-1-yl]benzenesulfonamide;
4-[5-(4-(2,3-dichlorophenyl)phenyl)-3-(trifluoromethyl)-1H-pyrazol-1-yl]benzenesulfonamide;
4-[5-(4-(3,5-dimethylphenyl)phenyl)-3-(trifluoromethyl)-1H-pyrazol-1-yl]benzenesulfonamide;
4-[5-(4-(2,4,5-trichlorophenyl)phenyl)-3-(trifluoromethyl)-1H-pyrazol-1-yl]benzenesulfonamide 4-[5-(4-(4-trifluoromethylphenyl)phenyl)-3-(trifluoromethyl)-1H-pyrazol-1-yl]benzenesulfonamide;
4-[5-(2-phenanthrenyl)-3-(trifluoromethyl)-1H-pyrazol-1-yl]benzenesulfonamide;
4-[5-(3-indolyl)-3-(trifluoromethyl)-1H-pyrazol-1-yl]benzenesulfonamide;
4-[5-(2-pyrrolyl)-3-(trifluoromethyl)-1H-pyrazol-1-yl]benzenesulfonamide;
4-[5-(4-benzylphenyl)-3-(trifluoromethyl)-1H-pyrazol-1-yl]benzenesulfonamide;
4-[5-(4-azidophenyl)-3-(trifluoromethyl)-1H-pyrazol-1-yl]benzenecarboxyamide;
4-[5-(4-(2-azidoethyl)phenyl)-3-(trifluoromethyl)-1H-pyrazol-1-yl]benzenecarboxyamide;
4-[5-(4-(3-azidopropyl)phenyl)-3-(trifluoromethyl)-1H-pyrazol-1-yl]benzenecarboxyamide;
4-[5-(4-(4-azidobutyl)phenyl)-3-(trifluoromethyl)-1H-pyrazol-1-yl]benzenecarboxyamide;
4-[5-(4-(4-azidophenyl)phenyl)-3-(trifluoromethyl)-1H-pyrazol-1-yl]benzenecarboxyamide;
4-[5-(4-(4-azidomethylphenyl)phenyl)-3-(trifluoromethyl)-1H-pyrazol-1-yl]benzenecarboxyamide;
4-[5-(2,5-dimethylphenyl)-3-(trifluoromethyl)-1H-pyrazol-1-yl]benzenecarboxyamide;
4-[5-(4-propylphenyl)-3-(trifluoromethyl)-1H-pyrazol-1-yl]benzenecarboxyamide;
4-[5-(4-(2-bromoethyl)phenyl)-3-(trifluoromethyl)-1H-pyrazol-1-yl]benzenecarboxyamide;
4-[5-(4-(4-butylphenyl)phenyl)-3-(trifluoromethyl)-1H-pyrazol-1-yl]benzenecarboxyamide;
4-[5-(4-(4-methylphenyl)phenyl)-3-(trifluoromethyl)-1H-pyrazol-1-yl]benzenecarboxyamide;
4-[5-(4-(3-bromopropyl)phenyl)-3-(trifluoromethyl)-1H-pyrazol-1-yl]benzenecarboxyamide;
4-[5-(4-(4-bromobutyl)phenyl)-3-(trifluoromethyl)-1H-pyrazol-1-yl]benzenecarboxyamide;
4-[5-(4-(4-bromomethylphenyl)phenyl)-3-(trifluoromethyl)-1H-pyrazol-1-yl]benzenecarboxyamide;
4-[5-(4-(4-tert-butylphenyl)phenyl)-3-(trifluoromethyl)-1H-pyrazol-1-yl]benzenecarboxyamide;
4-[5-(9-anthryl)-3-(trifluoromethyl)-1H-pyrazol-1-yl]benzenecarboxyamide;
4-[5-(2-fluorenyl)-3-(trifluoromethyl)-1H-pyrazol-1-yl]benzenecarboxyamide;
4-[5-(4-(4-chlorophenyl)phenyl)-3-(trifluoromethyl)-1H-pyrazol-1-yl]benzenecarboxyamide;
4-[5-(4-(3,5-dichlorophenyl)phenyl)-3-(trifluoromethyl)-1H-pyrazol-1-yl]benzenecarboxyamide;
4-[5-(4-(2,3-dichlorophenyl)phenyl)-3-(trifluoromethyl)-1H-pyrazol-1-yl]benzenecarboxyamide;
4-[5-(4-(3,5-dimethylphenyl)phenyl)-3-(trifluoromethyl)-1H-pyrazol-1-yl]benzenecarboxyamide;
4-[5-(4-(2,4,5-trichlorophenyl)phenyl)-3-(trifluoromethyl)-1H-pyrazol-1-yl]benzenecarboxyamide;
4-[5-(4-(4-trifluoromethylphenyl)phenyl)-3-(trifluoromethyl)-1H-pyrazol-1-yl]benzenecarboxyamide;
4-[5-(2-phenanthrenyl)-3-(trifluoromethyl)-1H-pyrazol-1-yl]benzenecarboxyamide;
4-[5-(3-indolyl)-3-(trifluoromethyl)-1H-pyrazol-1-yl]benzenecarboxyamide;
4-[5-(2-pyrrolyl)-3-(trifluoromethyl)-1H-pyrazol-1-yl]benzenecarboxyamide; and
4-[5-(4-benzylphenyl)-3-(trifluoromethyl)-1H-pyrazol-1-yl]benzenecarboxyamide.

Derivatives are intended to encompass any compounds which are structurally related to the compounds of formulae I and II or which possess the substantially equivalent activity, as measured by the derivative's ability to induce apoptosis in rapidly proliferating cells without substantial COX-2 inhibition. By way of example, such compounds may include, but are not limited to, prodrugs thereof. Such compounds can be formed in vivo, such as by metabolic mechanisms.

The present invention also relates to therapeutic methods of inducing apoptosis in undesirable rapidly proliferating cells, which include, but are not limited to cancer cells. The methods comprise administering a therapeutically effective amount of a compound of formula I or II to a subject having a disorder or being predisposed to a disorder involving rapidly proliferating cells.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I. Alkyl radical substituents of the present invention may also be substituted with other groups such as azido, for example, azidomethyl, 2-azidoethyl, 3-azidopropyl and so on.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4-chlorophenyl, 2,5-chlorophenyl and so forth. "Haloalkylaryl" refers to aryl radicals that have a haloalkyl substituent. Examples of haloalkylaryls include such radicals as bromomethylphenyl, 4-bromobutylphenyl and so on. Carboxyamide refers to the group —$CONH_2$, and sulfonamide refers to the group —$SO_2NH_2$.

Also included in the family of compounds of formulae I and II are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formulae I and II may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of compounds of formulae I and II include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of formulae I and II. All of these salts may be prepared by conventional means from the corresponding compounds of formulae I and II by reacting, for example, the appropriate acid or base with the compound of formula I or II.

All examples disclosed herein are for illustrative purposes only and are not meant to limit the claimed invention in any way.

General Synthesis Procedures

A general scheme for the synthesis of the carboxyamide compounds of formula I is shown below. Detailed syntheses follow.

Scheme 1ª

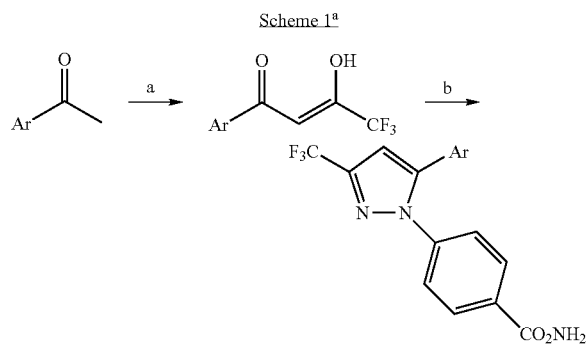

ª(a) 25% NaOCH₃/CH₃OH, MTBE, CF₃COOC₂H₅;
(b) (4-carbamoylphenyl)hydrazine·HCl, C₂H₅OH, reflux 4-[5-(4-Chlorophenyl)-3-(trifluoromethyl)-1H-pyrazol-1-yl]benzene-carboxyamide The title compound was synthesized via a two-step synthesis. Step a. The preparation of 4,4,4-trifluoro-1-(4-chlorophenyl)butane-1,3-dione was carried out as follows. To a solution of ethyl trifluoroacetate (1.08 g, 7.61 mmol) in 5 mL of methyl tert-butyl ether (MTBE) was added 25% sodium methoxide in methanol (1.8 mL) over 2 min. A solution of 4'-chloroacetophenone (1 g, 6.46 mmol) in 2 mL MTBE was added to the mixture dropwise over 5 min. After stirring for 16 h, 3 N HCl (3.4 mL) was added. The organic layer was collected, washed with brine, dried over magnesium sulfate, and concentrated to give a yellow-orange solid. Recrystallization from hexane yielded the dione (1.18 g, 86%). Step b. (4-Carbamoylphenyl)hydrazine hydrochloride (228 mg, 1.21 mmol) was added to a stirred solution of the aforementioned dione (300 mg, 1.21 mmol) in 20 mL of ethanol. The mixture was stirred under reflux for 24 h, cooled to room temperature, and concentrated to dryness. The residue was dissolved in ethyl acetate, washed with brine, dried over magnesium sulfate, and concentrated to give a light brown solid. Recrystallization from ethyl acetate and hexane gave the title compound (350 mg, 80%): $^1$H NMR (CDCl₃) δ □□□s, 1H), 7.16 (d, J=8.5 Hz, 2H), 7.34 (d, J=8.4 Hz, 2H), 7.40 (d, J=8.4 Hz, 2H), 7.83 (d, J=8.4 Hz, 2H); HRMS calc'd for M⁺ 365.0535. found 365.0522. Anal. ($C_{17}H_{11}ClF_3N_3O$) C, H, N.

4-[5-(2,4-Dichlorophenyl)-3-(trifluoromethyl)-1H-pyrazol-1-yl]benzene-carboxyamide. The title compound was synthesized from 2',4'-dichloroacetophenone using the two-step procedure described above in 52% overall yield. $^1$H NMR (CDCl₃) δ □□9s, 1H), 7.29 (d, J=2.0 Hz, 1H), 7.35 (d, J=8.6 Hz, 2H), 7.45 (d, J=2.0 Hz, 1H), 7.78 (d, J=8.6 Hz, 2H). HRMS calc'd for M⁺ 399.0145. found 399.0138. Anal. ($C_{17}H_{10}Cl_2F_3N_3O$) C, H, N.

4-[5-(2,5-Dichlorophenyl)-3-(trifluoromethyl)-1H-pyrazol-1-yl]benzene-carboxyamide. The title compound was synthesized from 2',5'-dichloroacetophenone using the two-step procedure described above in 60% overall yield. $^1$H NMR (CDCl₃) δ □□9s, 1 H), 7.35 (m, 5H), 7.80 (d, J=8.5 Hz, 2H); HRMS calc'd for M⁺ 399.0145. found 399.0150. Anal. ($C_{17}H_{10}Cl_2F_3N_3O$) C, H, N.

4-[5-(3,4-Dichlorophenyl)-3-(trifluoromethyl)-1H-pyrazol-1-yl]benzene-carboxyamide. The title compound was synthesized from 3',4'-dichloroacetophenone using the two-step procedure described above in 55% overall yield. $^1$H NMR (DMSO-d₆) δ 7.37s, 1H), 7.55 (d, J=8.5 Hz, 2H), 7.66 (d, J=8.5 Hz, 2H), 7.71 (d, J=2.0 Hz, 1H), 7.95 (d, J=8.5 Hz, 2H); HRMS calc'd for M⁺ 399.0145. found 399.0162. Anal. ($C_{17}H_{10}Cl_2F_3N_3O$) C, H, N.

4-[5-(4-Methylphenyl)-3-(trifluoromethyl)-1H-pyrazol-1-yl]benzene-carboxyamide. The title compound was synthesized from 4'-methylacetophenone using the two-step procedure described above in 65% overall yield. $^1$H NMR (CDCl₃) δ 2.37 (s, 3 H), □□4s, 1H), 7.10 (d, J=8.2 Hz, 2H), 7.15 (d, J=8.2 Hz, 2H), 7.41 (dd, J=1.8, 6.7 Hz, 2H), 7.80 (dd, J=1.8, 6.7 Hz, 2H); HRMS calc'd for M⁺ 345.1081. found 345.1057. Anal. ($C_{18}H_{14}F_3N_3O$) C, H, N.

4-[5-(4-Trifluoromethylphenyl)-3-(trifluoromethyl)-1H-pyrazol-1-yl]benzene-carboxyamide. The title compound was synthesized from 4'-trifluoromethylacetophenone using the two-step procedure described above in 53% overall yield. $^1$H NMR (CDCl₃) δ 7.45s, 1H), 7.54 (d, J=8.0 Hz, 2H), 7.62 (d, J=8.0 Hz, 2H), 7.79 (d, J=8.4 Hz, 2H), 8.03 (d, J=8.4 Hz, 2H); HRMS calc'd for M⁺ 399.0791. found 399.0791. Anal. ($C_{18}H_{11}F_6N_3O$) C, H, N.

4-[5-(4-Ethylphenyl)-3-(trifluoromethyl)-1H-pyrazol-1-yl]benzene-carboxyamide. The title compound was synthesized from 4'-ethylacetophenone using the two-step procedure described above in 44% overall yield. $^1$H NMR (CDCl₃) δ 1.24 (t, J=7.6 Hz, 3H), 2.67 (q, J=7.6 Hz, 2H), 6.74s, 1H), 7.13 (dd, J=2.2, 6.2 Hz, 4H), 7.42 (d, J=8.5 Hz, 2H), 7.81 (d, J=8.5 Hz, 2H); HRMS calc'd for M⁺ 359.1238. found 359.1247. Anal. ($C_{19}H_{16}F_3N_3O$) C, H, N.

4-[5-(2,4-Dimethylphenyl)-3-(trifluoromethyl)-1H-pyrazol-1-yl]benzene-carboxyamide. The title compound was synthesized from 2',4'-dimethylacetophenone using the two-step procedure described above in 62% overall yield. $^1$H NMR (CDCl₃) δ 1.94 (s, 3H), 2.35 (s, 3 H), □65s, 1H), 7.03 (bs, 1H), 7.08 (t, J=8.2 Hz, 2H), 7.35 (d, J=8.6 Hz, 2H), 7.73 (d, J=8.6 Hz, 2H); HRMS calc'd for M⁺ 359.1238. found 359.1240. Anal. ($C_{19}H_{16}F_3N_3O$) C, H, N.

4-[5-(2,5-Dimethylphenyl)-3-(trifluoromethyl)-1H-pyrazol-1-yl]benzene-carboxyamide. The title compound was synthesized from 2',5'-dimethylacetophenone using the two-step procedure described above in 58% overall yield. $^1$H NMR (CDCl₃) δ 1.90 (s, 3H), 2.32 (s, 3 H), □65s, 1H), 7.08 (m, 3H), 7.36 (d, J=8.3 Hz, 2H), 7.73 (d, J=8.5 Hz, 2H); HRMS calc'd for M⁺ 359.1238. found 359.1268. Anal. ($C_{19}H_{16}F_3N_3O$) C, H, N.

4-[5-(3,5-Dimethylphenyl)-3-(trifluoromethyl)-1H-pyrazol-1-yl]benzene-carboxyamide. The title compound was synthesized from 3',5'-dimethylacetophenone using the two-step procedure described above in 56% overall yield. $^1$H NMR (CDCl₃) δ 1.91 (s, 3H), 2.34 (s, 3 H), □67s, 1H), 7.08

(m, 3H), 7.36 (d, J=8.3 Hz, 2H), 7.73 (d, J=8.5 Hz, 2H); HRMS calc'd for M+ 359.1238. found 359.1257. Anal. ($C_{19}H_{16}F_3N_3O$) C, H, N.

A general scheme for the syntheses of the sulfonamide compounds of formula II is shown in FIG. 1. Detailed syntheses follow.

Synthesis of 4-[5-(4-(4-trifluoromethylphenyl)phenyl)-3-(trifluoromethyl)-1H-pyrazol-1-yl]benzenesulfonamide. synthesis. Step a. The preparation of 4-(4-trifluoromethylphenyl)acetophenone was carried out as follows. To the mixture of 4-bromobenzotrifluoride (1.0 g, 4.4 mmol) and 4-acetylphenylboronic acid (0.739 g, 4.4 mmol), $Pd(OAc)_2$ (1.97 mg), $K_2CO_3$ (1.54 g), $Bu_4NBr$ (1.43 g) and $H_2O$ (7 mL) were added, The mixture was stirred under argon for 30 min, warmed to 70° C., and kept stirring for 1 hr. The solution was cooled to room temperature, diluted with water, extracted with ethyl acetate. The intermediate was purified by Silica gel chromatography with yield of 86%. Step b. To a cooled solution of ethyl trifluoroacetate (1.0 g, 7.04 mmol) in $CH_2Cl_2$, NaH (338 mg, 14.1 mmol) was added, stirred for 15 min., and then a solution of 4-(4-trifluoromethylphenyl) acetophenone (1.86 g, 7.04 mmol) in $CH_2Cl_2$ was added. The mixture was stirred at room temperature for 6 hrs, Silica gel chromatography afforded the 4,4,4-trifluoro-1-(4-(4-trifluoromethylphenyl)phenyl)butane-1,3-dione (2.1 g, 83% yield). Step c. (4-Sulfamoylphenyl) hydrazine hydrochloride (200 mg, 0.89 mmol) was added to a stirred solution of the above dione (320 mg, 0.89 mmol) in 20 mL of ethyl acetate, The mixture was headed to reflux and stirred for 24 hr. After cooling to room temperature, the reaction mixture was concentrated in vacuo. The residue was dissolved in ethyl acetate, washed with water and brine. The product was purified by chromatography to give the title compound (290 mg, 71% yield).

Synthesis of 4-[5-(4-butylphenyl)-3-(trifluoromethyl)-1H-pyrazol-1-yl]benzenesulfonamide. The title compound was synthesized via a two-step synthesis. Step a. To a cooled solution of ethyl trifluoroacetate (1.0 g, 7.04 mmol) in $CH_2Cl_2$, NaH (338 mg, 14.1 mmol) was added, stirred for 15 min., and then a solution of 4-butylacetophenone (1.23 g, 7.04 mmol) in $CH_2Cl_2$ was added. The mixture was stirred at room temperature for 6 hr. Silica gel chromatography gave 4,4,4-trifluoro-1-(4-butylphenyl)butane-1,3-dione (1.63 g, 85% yield). Step b. (4-Sulfamoylphenyl)hydrazine hydrochloride (200 mg, 0.89 mmol) was added to a stirred solution of the above dione (244 mg, 0.89 mmol) in 20 mL of ethyl acetate, The mixture was headed to reflux and stirred for 24 hr. After cooling to room temperature, the reaction mixture was concentrated in vacuo. The residue was dissolved in ethyl acetate, washed with water and brine. Silica gel chromatography gave the title compound (246 mg, 65% yield).

Synthesis of 4-[5-(2-phenanthrenyl)-3-(trifluoromethyl)-1H-pyrazol-1-yl]benzenesulfonamide. The title compound was synthesized according to the following scheme in multigram scales:

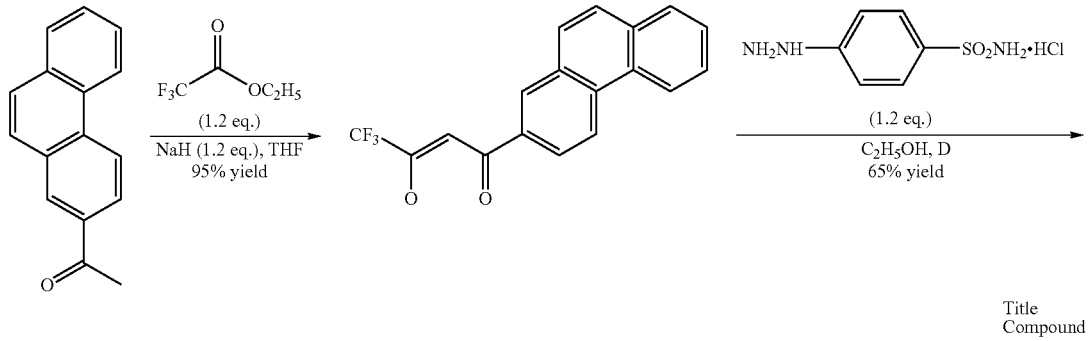

Claisen condensation of 2-acetylphenanthrene (Aldrich A1920-2) with ethyl trifluoroacetate (1.2 eq.) in the presence of NaH (1.2 eq.) afforded the 1,3-dicarbony adduct in 95% yield. Reaction with (4-sulfamoylphenyl)hydrazine hydrochloride provided the target molecule in 65% yeild. In the second step, use fo the HCl salt of the phenylhydrazine gave predominantly the 1,5-diarylpyrazole, and prevented the formation of the 1,3-diarylpyrozole isomer. (4-Sulfamoylphenyl)hydrazine hydrochloride was obtained from its sulfiamide counterpart in high yields. The identity and purity of individual intermediates and the final product were validated by $^1$H NMR, high resolution mass spectrometry, and HPLC analysis.

With regard to purification, the 1,3-dicarbonyl intermediate was purified by flash chromatography, and the final product can be isolated by crystallization from the reaction mixture with purity greater than 98%. Overall, the synthesis and purification procedures are straightforward and amenable to large-scale production.

EXAMPLES

Examples 1–13

Samples 1–13 were tested for their ability to induce apoptosis using the following procedure. Results are listed in Table 1 along with $IC_{50}$ values for the compounds.

Analysis for apoptosis Apoptosis ELISA. Induction of apoptosis was also assessed by using a "Cell Death Detection ELISA" assay (Boehringer-Mannheim) following the manufacturer's instructions. This test is based on the quantitative determination of cytoplasmic histone-associated DNA fragments in the form of mono- and oligonucleosomes after induced apoptotic death. In brief, PC-3 cells ($2.5 \times 10^6$) were plated on a T-75 flask 24 h before experiment. Cells were washed by 5 mL of serum-free RPMI 1640 medium twice, and were then treated with the test agent at different concentrations or DMSO vehicles for different time intervals. Both floating and adherent cells were collected, and cell lysates equivalent to $10^4$ cells were used for the ELISA analysis.

All compounds described herein were evaluated for their ability to induce apoptotic death in three separate cell lines, including androgen-dependent LNCaP (p53+/+), androgen-independent PC-3 (p53−/−), and Bcl-2-overexpressing PC-3 (PC-3/Bcl-2). The potency of individual compounds was expressed as $T_{1/2}$ that denotes the time required for eliciting 50% apoptotic death the indicated concentration. Results obtained with these cell lines were virtually identical, indicating that the induction of apoptosis was independent of androgen sensitivity, p53 functional status, and Bcl-2 expressing levels.

TABLE 1

Apoptosis induction and COX-2 inhibition for several inventive compounds

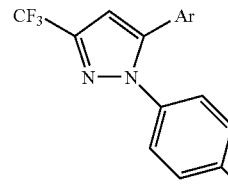

| Example No. | $R^5$ | Ar | $T_{1/2}$ (h), 50 μM | $IC_{50}$ (μM) |
|---|---|---|---|---|
| 1 | —CONH$_2$ | 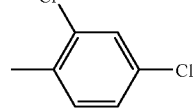 | 2 | |
| 2 | —CONH$_2$ | 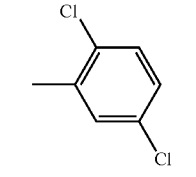 | 3 | |
| 3 | —CONH$_2$ | 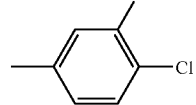 | 1.5 | |
| 4 | —CONH$_2$ | 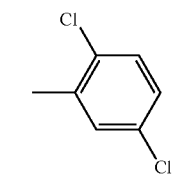 | 1.5 | |
| 5 | —SO$_2$NH$_2$ | 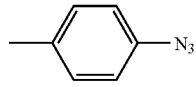 | 3 | >100 |
| 6 | —SO$_2$NH$_2$ |  | 1.5 | |

TABLE 1-continued

Apoptosis induction and COX-2 inhibition for several inventive compounds

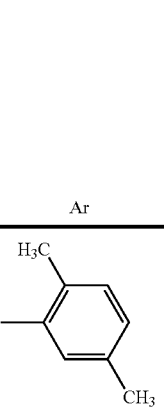

| Example No. | R⁵ | Ar | $T_{1/2}$ (h), 50 μM | $IC_{50}$ (μM) |
|---|---|---|---|---|
| 7 | —SO$_2$NH$_2$ | 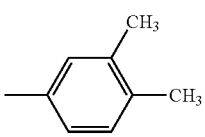 | 1 | >100 |
| 8 | —SO$_2$NH$_2$ | 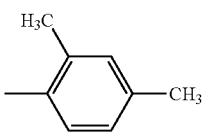 | 2 | |
| 9 | —SO$_2$NH$_2$ | 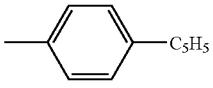 | 2 | 0.12 |
| 10 | —SO$_2$NH$_2$ | 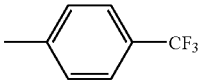 | 2.5 | 0.86 |
| 11 | —SO$_2$NH$_2$ | —⟨⟩—CF$_3$ | 3 | 8.23 |
| 12 | —SO$_2$NH$_2$ | 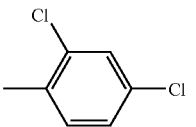 | 2 | 0.056 |
| 13 | —SO$_2$NH$_2$ | 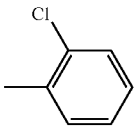 | 4 | 0.01 |

Examples 14–71

Compounds of the present invention were tested on the following cell lines by the National Cancer Institute Developmental Therapeutics Program.

| Examples 14–19 | Leukemia |
|---|---|
| | CCRF-CEM |
| | HL-60 |
| | K-562 |
| | MOLT-4 |
| | RPMI-8826 |
| | SR |

-continued

| Examples 20–28 | Non-small cell lung cancer |
|---|---|
| | A549/ATCC |
| | EKVX |
| | HOP-62 |
| | HOP-92 |
| | NCI-H226 |
| | NCI-H23 |
| | NCI-H322M |
| | NCI-H460 |
| | NCI-522 |

-continued

| | |
|---|---|
| Examples 29–34 | Colon cancer |
| | COLO 205 |
| | HCT-116 |
| | HCT-15 |
| | HT29 |
| | KM12 |
| | SW-620 |
| Examples 35–40 | CNS cancer |
| | SF-268 |
| | SF-295 |
| | SF-539 |
| | SNB-19 |
| | SNB-75 |
| | U251 |
| Examples 41–47 | Melanoma |
| | LOX IMVI |
| | MALME-3M |
| | M14 |
| | SK-MEL-2 |
| | SK-MEL-5 |
| | UACC-257 |
| | UACC-62 |
| Examples 48–53 | Ovarian cancer |
| | IGROV1 |
| | OVCAR-3 |
| | OVCAR-4 |
| | OVCAR-5 |
| | OVCAR-8 |
| | SK-OV-3 |
| Examples 54–61 | Renal Cancer |
| | 786-0 |
| | A498 |
| | ACHN |
| | AKI-1 |
| | RXF 393 |
| | SN12C |
| | TK-10 |
| | UO-31 |
| Examples 62–63 | Prostate cancer |
| | PC-3 |
| | DU-145 |
| Examples 64–71 | Breast cancer |
| | MCF-7 |
| | NCI/ADR-RES |
| | MDA-MB-231/ATCC |
| | HS 578T |
| | MDA-MB-435 |
| | MDA-N |
| | BT-549 |
| | T-47D |

The present invention comprises a pharmaceutical composition for inducing apoptosis in undesirable, rapidly proliferating cells, such as for treating, preventing, or delaying the onset of a cancer in a subject in need of such treatment. The pharmaceutical composition comprises a therapeutically effective amount of a compound of formula I or II, or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intra-vascularly, intraperitoneally, intranasal, intrabronchial, subcutaneously, intramuscularly or topically (including aerosol). With some subjects local administration, rather than system administration, may be preferred. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the apoptosis-inducing compounds of the present invention may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors including batiastat, marimastat, Agouron Pharmaceuticals AG-3340, and Roche RO-32-3555, or $\alpha_v\beta_3$ inhibitors may be used. Suitable agents which may be used in combination therapy will be recognized by those of skill in the art. Similarly, when combination therapy is desired, radioprotective agents known to those of skill in the art may also be used.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

If the unwanted proliferating cells are localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol exipients, such as saline, and administered using commercially available nebulizers. Formulation in a fatty acid source may be used to enhance biocompatibility.

For rectal administration, the active ingredient may be formulated into suppositories using bases which are solid at room temperature and melt or dissolve at body temperature. Commonly used bases include cocoa butter, glycerinated gelatin, hydrogenated vegetable oil, polyethylene glycols of various molecular weights, and fatty esters of polyethylene stearate.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

CYCLOOXYGENASE-2, PLAYER OR SPECTATOR IN CYCLOOXYGENASE-2 INHIBITOR-INDUCED APOPTOSIS IN PROSTATE CANCER CELLS

Background: The antitumor activity of cyclooxygenase-2 (COX-2) inhibitors is thought to involve COX-2 enzyme inhibition and apoptosis induction, although whether COX-2 inhibition is required for apoptosis is unresolved. Different COX-2 inhibitors have similar $IC_{50}$ values (concentration for 50% inhibition) for COX-2 inhibition but differ considerably in their ability to induce apoptosis, suggesting that a COX-2-independent pathway might be involved in apoptosis. To test this hypothesis, we investigated the effect of COX-2 depletion on apoptosis and performed a structure-activity analysis of the COX-2 inhibitor celecoxib in the androgen-independent prostate cancer cell line PC-3. Methods: Tet-On COX-2 antisense clones were isolated to assess the effect of COX-2 expression on cell viability and sensitivity to apoptosis induction by COX-2 inhibitors. Untreated Tet-On clones differentially expressed COX-2, and doxycycline-treated clones were depleted of COX-2. We synthesized and characterized various celecoxib analogues with various COX-2 inhibitory activities and determined their apoptotic activity in PC-3 cells. Apoptosis was assessed with four tests. All statistical tests are two-sided.

Results: In contrast to the effect of COX-2 inhibitors, which induced apoptosis, COX-2 depletion did not induce cell death. Susceptibility to COX-2 inhibitor-induced apoptosis was independent of the level of COX-2 expression. Structure-activity analysis found no correlation between apoptosis induction and COX-2 inhibition. Some derivatives of the parent compound that lacked COX-2 inhibitory activity facilitated apoptosis, and vice versa. Moreover, celecoxib and apoptosis-active celecoxib derivatives mediated cell death by inhibiting Akt and ERK2 signaling.

Conclusion: We have dissociated the apoptosis-inducing activity from the COX-2 inhibitory activity by structural modifications of the COX-2 inhibitor celecoxib. This separation of activities may provide a molecular basis for the development of new classes of apoptosis-inducing agents.

The signaling mechanism used by cyclooxygenase-2 (COX-2) inhibitors to mediate apoptotic death in cancer cells has been the focus of many investigations (1–10). A crucial issue yet to be resolved is whether COX-2 inhibition plays an obligatory role in the induction of apoptosis by COX-2 inhibitors (11). The premise that COX-2 inhibition is integral to the antitumor effect is based on the assumption that prostaglandins and other COX-2-generated downstream mediators promote tumor cell proliferation, survival, and angiogenesis in an autocrine and/or paracrine manner (12–16). It has been reported that COX-2 overexpression leads to the inhibition of apoptosis or altered cell cycle kinetics in epithelial cells of the gastrointestinal system (17,18) and in PC-12 pheochromocytoma cells (19). In addition, knockout of the COX-2 gene can suppress tumorigenesis in mice with a genetic predisposition for polyp formation (20). Animal studies demonstrate that efficient tumor growth required the presence of COX-2 in tumor host (8) and that enhanced COX-2 expression was sufficient to induce mammary gland tumorigenesis (21). On the other hand, several lines of evidence indicate that a COX-2-independent mechanism may be involved in the antitumor effect of COX-2 inhibitors. For example, sulindac metabolites, which do not inhibit COX activity, induced apoptosis in prostate cancer cells with high potency (22). In contrast to gastrointestinal cells and PC-12 cells, COX-2 overexpression in immortalized human umbilical vein endothelial, HEK-293, COX-7, and NIH 3T3 cells led to increased cell death and/or cell cycle arrest (23,24). The dichotomous effect of COX-2 overexpression on cell growth may, in part, be attributable to physiologic differences among different cell types. Moreover, malignant transformation in embryo fibroblasts was reportedly independent of the status of COX expression.

Previously, we demonstrated that celecoxib induced apoptosis in prostate cancer cells by interfering with multiple signaling targets including Akt, ERK2, and endoplasmic reticulum $Ca^{2+}$-ATPases (10,25). Disruption of these signaling pathways leads rapidly to apoptosis, a mechanism distinctly different from that of conventional anticancer agents. It is noteworthy that the effect of celecoxib on apoptosis was independent of androgen responsiveness, the level of Bcl-2 expression, and the functional status of p53 in cancer cells (10,25). Nevertheless, this rapid induction of apoptosis was unique to celecoxib because the potency of other COX-2 inhibitors, including rofecoxib, NS398, and DuP697, to induce apoptosis was much lower than that of celecoxib (25). This discrepancy underscores differences in the mechanisms by which these COX-2 inhibitors mediate apoptosis in prostate cancer cells. To sort out the issue of whether COX-2 inhibitor-induced apoptosis required the inhibition of COX-2 enzyme activity, we examined the effect of COX-2 depletion on apoptosis in tetracycline-on (Tet-On) antisense COX-2 PC-3 clones and performed a structure-activity analysis of various celecoxib derivatives in androgen-independent PC-3 prostate cancer cells.

Cells and reagents We used three different prostate cancer cell lines to assess the impact of androgen responsiveness and p53 functional status on the induction of apoptosis by celecoxib and its derivatives. The cell lines used included androgen-responsive LNCaP ($p53^{+/+}$) and androgen-nonresponsive PC-3 and DU-145 (both $p53^{-/-}$). The antisense COX-2 construct was a gift from Drs. Rebecca Chinery and Jason Morrow (Vanderbilt University Medical School). It contained an almost complete human COX-2 insert (1.93 kilobases) that was cloned into the XbaI/EcoRV sites in the TRE (tetracycline response element)-response plasmid pUHD.2neo (26). This tetracycline-inducible antisense COX-2 construct has been used in colorectal cancer cells to assess the role of prostaglandins in cell proliferation (26). Celecoxib and rofecoxib were obtained from commercial capsules by solvent extraction followed by recrystallization. DuP697 was a gift from Professor Hsin-Hsiung Tai (University of Kentucky), and NS398 was obtained from Calbiochem (La Jolla, Calif.). 4-[5-(4-Chlorophenyl)-3-(trifluoromethyl)-1H-pyrazol-1-yl] benzenesulfonamide (compound 1), 4-[5-phenyl-3-(trifluoromethyl)-1H-pyrazol-1-yl]benzenesulfonamide (compound 2), 4-[5-(4-aminophenyl)-3-(trifluoromethyl)-1H-pyrazol-1-yl]benzenesulfonamide (compound 3), 4-[5-(4-ethylphenyl)-3-(trifluoromethyl)-1H-pyrazol-1-yl]benzenesulfonamide (compound 4), 4-[5-(4-trifluoromethylphenyl)-3-(trifluoromethyl)-1H-pyrazol-1-yl]benzenesulfonamide (compound 5), 4-[5-(2,5-dichlorophenyl)-3-(trifluoromethyl)-1H-pyrazol-1-yl]benzenesulfonamide (compound 6), 4-[5-(2,5-dimethylphenyl)-3-(trifluoromethyl)-1H-pyrazol-1-yl] benzenesulfonamide (compound 7) were synthesized according to published procedures (27). Rabbit anti-COX-2 antibodies were obtained from Cayman Chemical Co. (Ann Arbor, Mich.). Rabbit polyclonal antibodies against Akt, phospho-$Ser^{473}$-Akt, ERK, and phospho-ERK were purchased from New England Biolabs (Beverly, Mass.), and mouse anti-actin monoclonal antibody was from ICN (Costa Mesa, Calif.). Goat anti-rabbit IgG-horseradish peroxidase conjugates were purchased from Jackson ImmunoResearch (West Groove, Pa.). Rabbit anti-poly(ADP-ribose) polymerase (PARP) antibodies were from PharMingen (San Diego, Calif.).

Development of PC-3 Tet-On antisense COX-2 clones PC-3 cells were cultured in RPMI 1640 medium supplemented with 10% fetal bovine serum (FBS) in T-25 flasks at 37° C. in a humidified $CO_2$ incubator to 80% confluency. Each flask was washed with 6 mL of serum-free Opti-MEM (Invitrogen Life Technologies; Carlsbad, Calif.), and then 3 mL of serum-free Opti-MEM was added. Aliquots containing 0.12 μg of the Tet-On regulator plasmid pTet-On (Clontech; Palo Alto, Calif.) and 0.12 μg of the antisense COX-2 construct in 150 μL of serum-free OPTI-MEM medium were preincubated with 3 μL of the Plus reagent from the LipofectAMINE Plus Reagent kit (Invitrogen Life Technologies) at 25° C. for 15 minutes, followed by 12 μL of the LipofectAMINE reagent in 150 μL of Opti-MEM medium. The resulting mixture was incubated at 25° C. for 15 minutes and then added to each flask with gentle mixing. After 5 hours at 37° C., the transfection medium was replaced with 5 mL of RPMI 1640 medium containing 10% Tet-System-approved FBS (Clontech). After 48 hours, cells were cultured in fresh medium containing G418 at 100 μg/mL to select for transfected clones. The G418-supplemented medium was changed every 4 days. After 3 weeks, G418-resistant cells were subcloned into 96-well plates by limiting dilution with a final cell density of about 0.5 cell per well. After 12 days with a change of G418-containing medium every 4 days, viable clones were further subcloned into 12-well plates. After 4 or 5 days, cells in each well were divided into three T-25 flasks. The level of COX-2 expression was determined 120 hours after cells were exposed to doxycycline (2 μg/mL) by western blot analysis. By this procedure, the following four independent clones (2F6, 1F2, 3D9, and 7D9) were selected for analyses: 2F6 was a COX-2-deficient clone, and 1F2, 3D9 7D9 expressed different levels of COX-2 in the absence of doxycycline.

Immunoblotting For western blot analysis, cells were washed in phosphate-buffered saline (PBS), resuspended in sodium dodecyl sulfate (SDS) gel-loading buffer consisting of 50 mM Tris-HCl, pH 6.8, 100 mM dithiothreitol, 2% SDS, 0.1% bromophenol blue, and 10% glycerol, sonicated with an ultrasonic sonicator for 5 seconds (Virsonic 300, 4.5 output), and boiled for 5 minutes. After a brief centrifugation, equivalent protein amounts (60–100 μg) from the soluble fractions were resolved in 10% SDS-polyacrylamide gels on a Minigel apparatus and transferred to a nitrocellulose membrane in a semidry transfer cell. The transblotted membrane was washed twice with Tris-buffered saline (TBS) containing 0.05% Tween 20 (TBST). After blocking with TBS containing 5% nonfat milk for 60 minutes, the membrane was incubated with the appropriate primary antibody (anti-COX-2, anti-Akt, anti-P-$^{473}$Ser Akt, anti-ERK, and anti-phospho-ERK antibodies diluted 1:1,000; anti-actin monoclonal antibody, diluted 1:5,000) in TBS-1% nonfat milk at 4° C. for 12 hours and washed twice with TBST. The membranes were probed with goat anti-rabbit IgG-horseradish peroxidase conjugates (diluted 1:5,000) for 1 hour at room temperature and washed twice with TBST. Bands were visualized by enhanced chemiluminescence.

Prostaglandin $E_2$ ($PGE_2$) immunoassay Parental and transfected cells with or without a doxycycline (2 μg/mL) pretreatment were grown to $10 \times 10^6$ cells in T-75 flasks in 10% FBS-supplemented RPMI 1640 medium with or without a doxycycline. Culture medium was changed, and 24 hours later conditioned medium was collected to assay $PGE_2$. Conditioned medium was centrifuged to remove particulate material, and then cells were collected by scraping to determine the protein concentration. $PGE_2$ was assayed in 100 μL medium in triplicate according to the manufacturer's instruction (R&D Systems, Inc.; Minneapolis, Minn.). $PGE_2$ data were normalized to protein content.

Cell viability Parental or transfected PC-3 cells with or without doxycycline (2 µg/mL) pretreatment were plated in 12-well plates and cultured in RPMI 1640 medium supplemented with 10% FBS in the absence or presence of 2 µg/mL doxycycline for 48 hours. Various concentrations of COX-2 inhibitors dissolved in dimethyl sulfoxide (DMSO; final concentration, 0.1%) were then added to the cells in serum-starved RPMI 1640 medium. Control cells received DMSO vehicle at the same concentration. During treatment, the percentage of floating cells increased over time. At the end of the treatment, adherent cells were harvested by trypsinization, and floating cells were recovered by centrifugation at 3,200×g for 5 minutes. Cell morphology was assessed with a light microscope at ×400. Both adherent and floating cells were combined, and cell viability was assessed by trypan blue dye exclusion.

Analysis for Apoptosis

In addition to the surface morphologic changes observed by phase-contrast microscopy, four methods were used to assess drug-induced apoptotic cell death.

Phosphatidylserine externalization. Approximately $2.5 \times 10^5$ cells were grown on glass coverslips for 24 hours. At various times after drug treatment, cells were washed gently with PBS and then exposed to 0.5 mL of binding buffer (10 mM HEPES [pH 7.4], containing 150 mM NaCl, 2.5 mM $CaCl_2$, 1 mM $MgCl_2$, and 4% bovine serum albumin), followed by 0.6 mL of annexin V-fluorescein isothiocynate (FITC) (200 µg/mL) for 30 minutes. After washing with binding buffer, apoptotic cells were identified directly as cells with annexin V-FITC on their outer membrane under a fluorescence microscope. In a set of controls, cells received medium containing DMSO vehicle in lieu of the test agent.

4',6-Diamidino-2-phenylindole (DAPI) staining of nuclei. At various times after treatment with different test agents, morphologic changes were detected in nuclei of apoptotic cells by staining with the DNA binding fluorochrome DAPI. For adherent PC-3 cells, cells were grown on glass coverslips until approximately 70% confluent and exposed to the test agent at 50 µM for various times. Supernatants then were carefully removed, adherent cells were washed with PBS, DAPI (0.5 µg/mL) was added in a fixation solution (4% paraformaldehyde, 2 mM EGTA [ethylene glycol bis (β-aminoethyl ether)-N,N,N'N'-tetraacetic acid], and 13.7% sucrose in PBS), and the mixture was incubated at room temperature for 20 minutes in the dark. Cells were then washed for two 20-minute periods with PBS. Floating PC-3 cells were examined by a modification of the above method. PC-3 cells were cultured in T-25 flasks and treated with the test agent. Floating cells then were collected, washed, and stained with DAPI as described above. Cells were allowed to attach to poly-L-lysine-coated coverslips and viewed by microscopy at a magnification of 400×.

Apoptosis detection by an enzyme-linked immunsorbent assay (ELISA). Induction of apoptosis was also assessed by using a "Cell Death Detection ELISA" assay (Boehringer-Mannheim) by following the manufacturer's instructions. This test is based on the quantitative determination of cytoplasmic histone-associated DNA fragments in the form of mono- and oligonucleosomes after induced apoptotic death. In brief, $2.5 \times 10^6$ PC-3 cells were cultured in a T-75 flask 24 hours before the experiment. Cells were washed twice in 5 mL of serum-free RPMI 1640 medium and then treated with a test agent or the DMSO vehicle as indicated. Both floating and adherent cells were collected, and cell lysates equivalent to $10^4$ cells were used in the ELISA.

Western blot analysis of PARP cleavage. Drug-treated cells were collected, washed with ice-cold PBS, and resuspended in lysis buffer [20 mM Tris-HCl (pH 8), 137 mM NaCl, 1 mM $CaCl_2$, 10% glycerol, 1% Nonidet P-40, 0.5% deoxycholate, 0.1% sodium dodecyl sulfate, 100 µM 4-(2-aminoethyl)benzenesulfonyl fluoride, leupeptin at 10 µg/mL, and aprotinin at 10 µg/mL]. Soluble cell lysates were collected after centrifugation at 1,500×g for 5 minutes. Equivalent amounts of protein (60–100 µg) from each lysate were resolved in 10% SDS-polyacrylamide gels. Bands were transferred to nitrocellulose membranes and analyzed by immunoblotting with anti-PARP antibodies, as described above.

Statistical analysis Each experiment was performed in triplicate. All experiments were carried out at least two times on different occasions. Where appropriate, the data are presented as the mean ±95% confidence interval.

Figure 2:
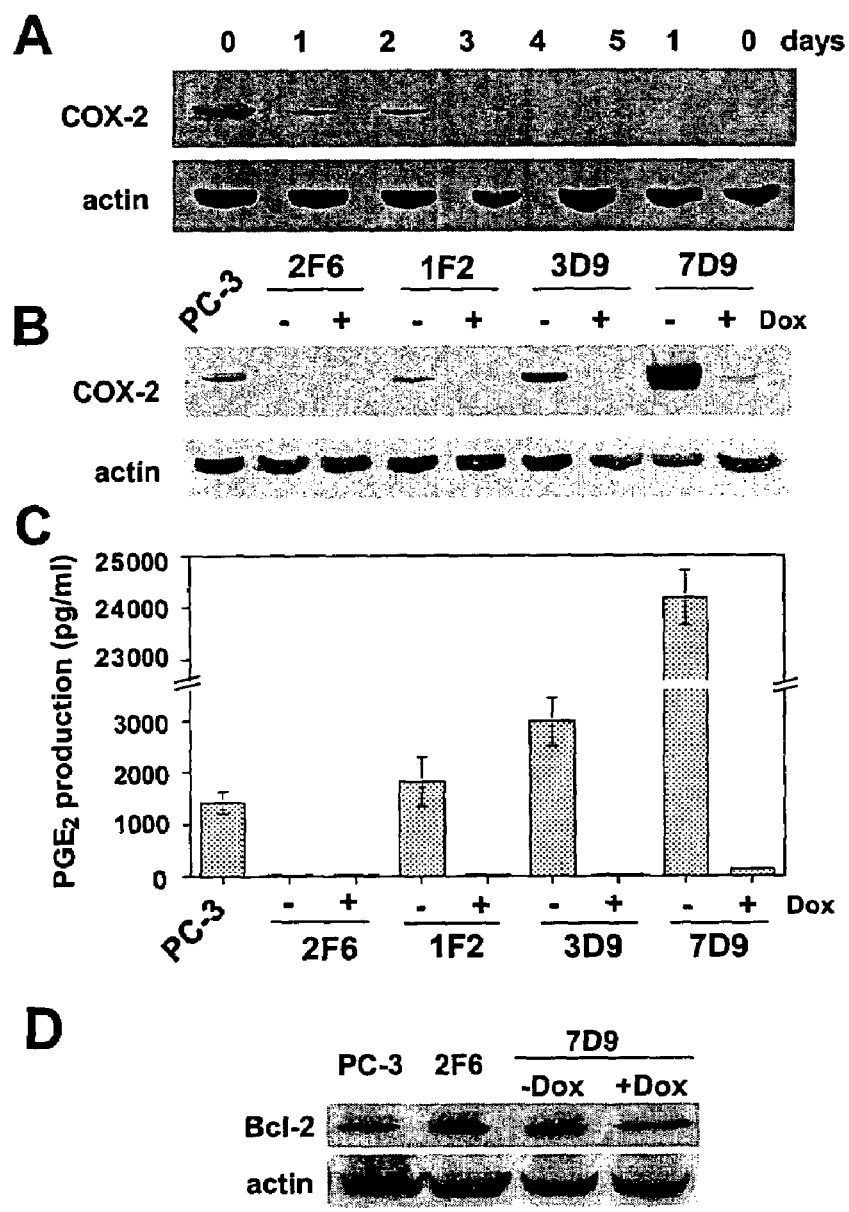
FIG. 2A depicts a Western blot analysis showing the time course of COX-2 depletion in the antisense COX-2 clone 3D9 in response to doxyclycline.
FIG. 2B depicts a Western blot analysis showing the COX-2 protein levels in parental PC-3 cells and four independent antisense COX-2 clones in the presence (+) or absence (−) of doxycycline (Dox; 2 μg/mL) for 10 days.
FIG. 2C shows Prostaglandin $E_2$ ($PGE_2$) production in parental PC-3 cells and four antisense COX-2 clones without (−) or with (+) doxycycline pretreatment as indicated.
FIG. 2D shows the level of Bcl-2 expression in parental PC-3 cells, 2F6D cells (no doxycycline treatment), and 7D9 cells in the presence (+) or absence (−) of doxycycline (2 μg/mL) for 10 days.

Isolation and Characterization of Tet-On Antisense COX-2 Clones To assess the effect of COX-2 enzyme activity on cell growth, we prepared Tet-On antisense COX-2 clones by transfecting parental PC-3 cells with an antisense COX-2 cDNA construct under the control of a tetracycline-inducible promoter. Four Tet-On antisense COX-2 clones, 2F6, 1F2, 3D9, and 7D9, were selected after subcloning the G418-resistant cells by limiting dilution. 2F6 is a COX-2-deficient clone in which the COX-2 protein was virtually undetectable, and 1F2, 3D9, and 7D9 are antisense COX-2 clones. In these clones, in the absence of doxycycline, COX-2 is differentially expressed, but in the presence of doxycycline, COX-2 is depleted (FIG. 2B). FIG. 2A shows a western blot analysis of the effect of doxycycline (2 µg/mL) on COX-2 expression in the Tet-On clone 3D9 over a 10-day period. By 4 days after the addition of doxycycline, COX-2 protein had been depleted in 3D9 cells, and as long as doxycycline was present, COX-2 was not detected. Because COX-1 expression was negligible in these clones (data not shown), COX-2 was the major producer of prostaglandins. Accordingly, the level of COX-2 expression reflected the level of $PGE_2$ production. Although the levels of $PGE_2$ in 1F2 cells and parental PC-3 cells were comparable, those in 3D9 were twofold higher and those in 7D9 cells were 10-fold higher than levels in parental cells (FIG. 2C). However, when treated with rofecoxib, NS398, or DuP697 at 50 µM, $PGE_2$ production was reduced to the same extent in 1F2, 3D9, and 7D9 cells and parental PC-3 cells (data not shown; $PGE_2$ in celecoxib-treated cells could not be determined due to rapid apoptosis). Because the decreased expression of the antiapoptotic protein Bcl-2 has been implicated in the apoptotic mechanism of the COX-2 inhibitors SC-58125 and NS-398 (1,2), it is also noteworthy that COX-2 ablation had essentially no impact on the expression of Bcl-2 (FIG. 2D).

COX-2 Ablation and Consequent Effect on Apoptosis in Prostate Cancer Cells

Using these COX-2 antisense clones, we obtained two lines of evidence that the effect of COX-2 inhibitors on apoptosis was independent of their COX-2-inhibitory activity. First, although both antisense COX-2 cDNA and COX-2 inhibitors completely blocked prostaglandin production, their effects on cell viability were markedly different. Treatment of PC-3 cells or any of the four clones with individual COX-2 inhibitors led to apoptotic death, whereas depletion of COX-2, and thus inhibition of $PGE_2$ production, with the antisense cDNA did not adversely affect the viability of these antisense clones; i.e., this treatment did not induce cell death.

Figure 3:
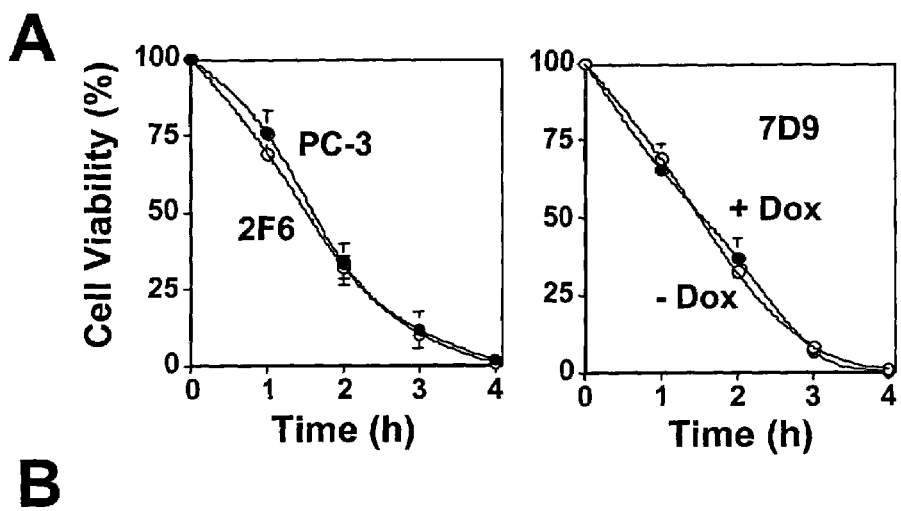
FIG. 3A shows a graph of the effect of 50 μM celecoxib on cell viability for PC-3 cells and the COX-2 deficient clone 2F6, left, and a graph of the effect of 50 μM celecoxib on cell viability for the COX-2 antisense clone 7D9 with and without doxycycline pretreatment.
FIG. 3B shows Western blots showing the phoshorylation status of Akt and ERK2 in the COX-2 antisense clone 7D9 with and without doxycycline.
Figure 3:
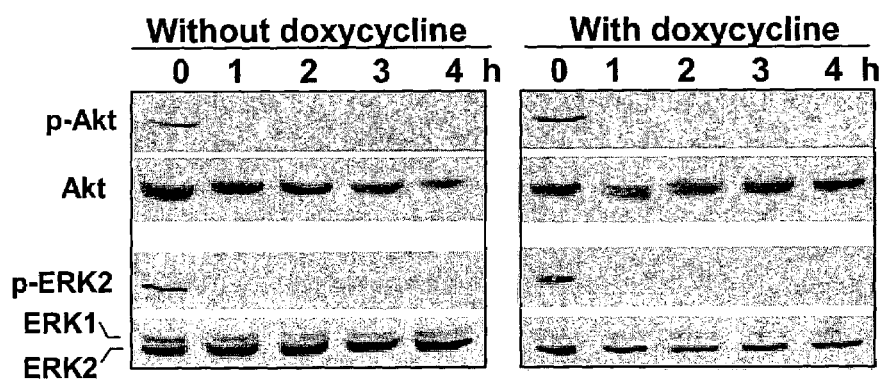

Second, although the basal levels of COX-2 in these four clones varied, all clones and parental PC-3 cells were equally susceptible to apoptosis induced by COX-2 inhibitors, and this susceptibility did not change after doxycycline-induced COX-2 depletion. In other words, susceptibility to COX-2 inhibitor-induced apoptosis was independent of the level of COX-2 expression. FIG. 3A shows the time course of cell death in the presence of 50 μM celecoxib in PC-3 cells, COX-2-deficient 2F6 cells, and COX-2-overexpressing 7D9 cells with and without COX-2 depletion. The time required for 50% cell death ($T_{1/2}$) of all the clones incubated with 50 μM celecoxib was approximately 2 hours. Similar results were noted with 1F2 and 3D9 cells.

Previously, we demonstrated that celecoxib induced rapid apoptotic death in both androgen-responsive LNCaP ($p53^{+/+}$) and androgen-nonresponsive PC-3 ($p53^{-/-}$) prostate cancer cells by inhibiting the Akt and ERK signaling pathways (10,25). In this study, the apoptotic death induced in all four clones was also associated with decreased phosphorylation of Akt and ERK2, as observed in parental PC-3 cells, and the time course for the dephosphorylation of Akt and ERK2 in 7D9 cells (FIG. 2B) was consistent with that for cell death. Similar results were obtained with the three other clones.

Figure 4:
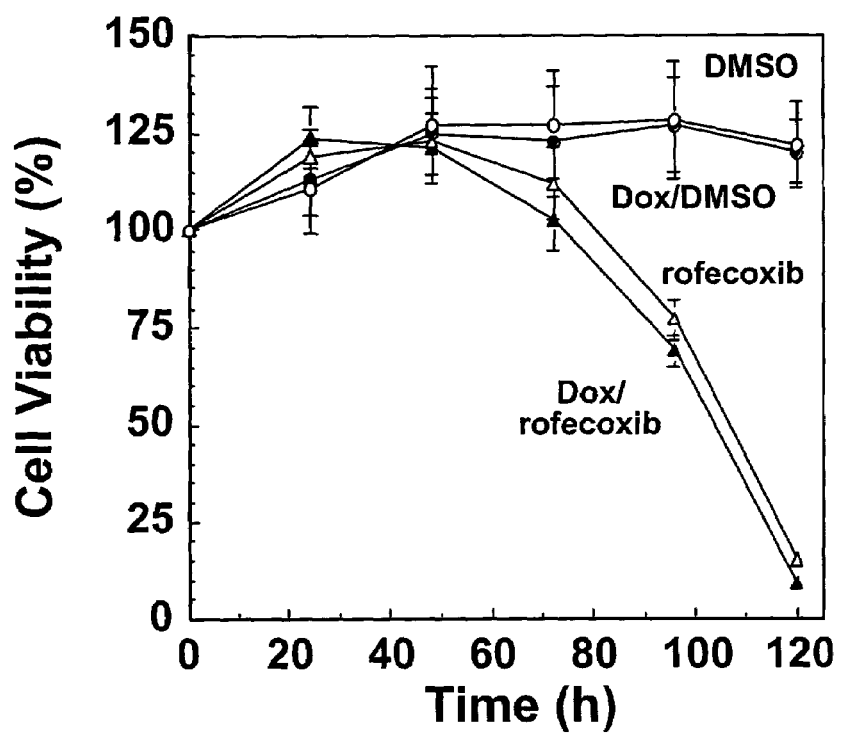
FIG. 4 is a graph of Cell Viability versus Time showing the effect of rofecoxibn and the dimethylsulfoxide vehicles on the viability of the COX-2 antisense clone 7D9 with and without doxycycline treatment.

The effect of COX-2 depletion on apoptosis induced by three other COX-2 inhibitors, rofecoxib, NS398, and DuP697, was also examined in the COX-2 antisense clones. These compounds triggered apoptosis in parental PC-3 cells by a mechanism distinctly different from that of celecoxib (25). The onset of apoptosis was significantly delayed vis-à-vis celecoxib, with $T_{1/2}$ values for rofecoxib, NS398, or DuP697 (each at 100 μM) ranging from 96 hours to 120 hours. FIG. 4 shows the cell viability after exposure of 7D9 cells to 100 μM rofecoxib with or without pretreatment with doxycycline. In line with the celecoxib data, loss of COX-2 expression did not alter the susceptibility of these clones to the induction of apoptosis by rofecoxib. Similar results were obtained with NS398 and DuP697 (data not shown).

Structure-Activity Analysis To further corroborate our hypothesis, structural modifications of celecoxib were carried out to dissociate COX-2 inhibition and the induction of apoptosis. We synthesized a series of celecoxib derivatives with different substituents at the terminal phenyl ring and examined the apoptosis-inducing potency of each. FIG. 5 summarizes the structures, the COX-2 inhibitory activity ($IC_{50}$=concentration of drug inhibiting COX-2 activity by 50%), and the apoptosis-inducing activity ($T_{1/2}$) of celecoxib and seven representative analogues.

Figure 6:
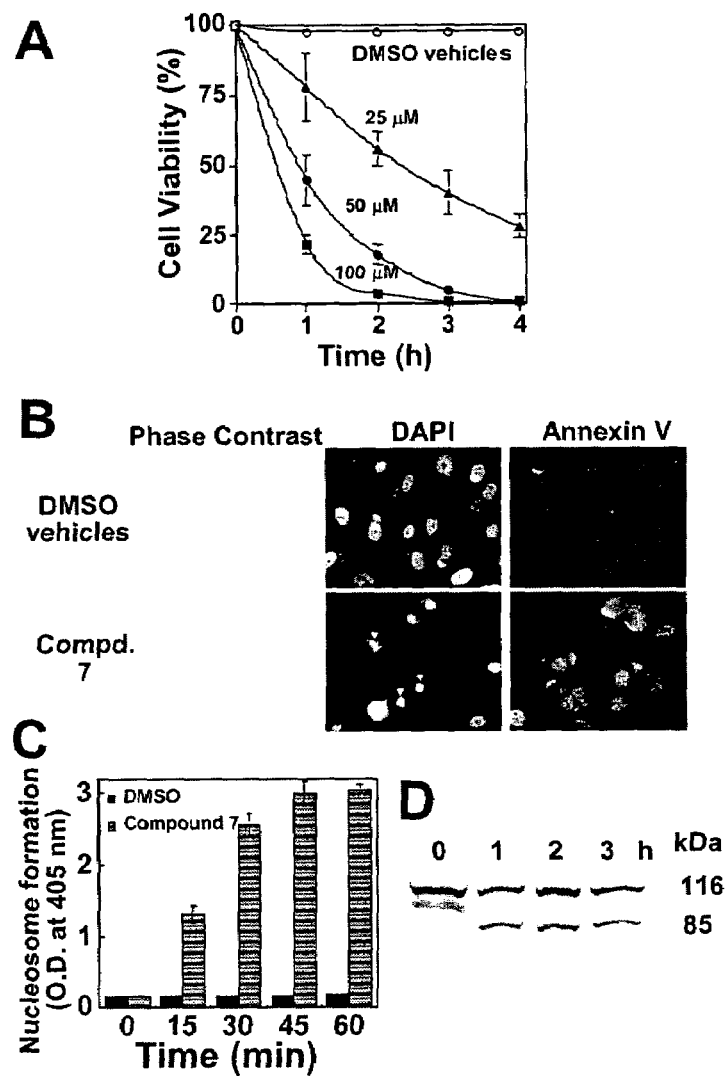
FIG. 6A shows dose and time-dependent effects of compound 7a on the cell viability of PC-3 cells.
FIG. 6B shows microscopy of cells after treatment with DMSO or 50 μM compound 7a. (Left) phase-contrast micrographs of PC-3 cells 2 hours after treatment, (center) fluorescence microscopy showing nuclear fragmentation, viewed after DNA staining with 4'-,6'-diamidino-2-phenylindole (DAPI), 2 hours after treatment, and (right) detection of annexin V binding to the surface of apoptotic cells by fluorescence microscopy for PC-3 cells one hour after treatment with compound 7a or DMSO.
FIG. 6C is a graph of Nucleosome formation (O.D. at 405 nm) versus Time for PC-3 cells treated with DMSO and compound 7a (50 μM).
FIG. 6D is a Western blot showing induction of PARP cleavage by compound 7a (50 μM) in PC-3 cells.

The structure-activity analysis found no correlation between the COX-2 inhibitory and apoptosis-inducing activities. Increased polarity (i.e., 4-amino in compound 3a) or bulkiness (i.e., 4-ethyl-, 4-trifluoromethyl-, 2,5-dichloro-, and 2,5-dimethyl- in compounds 4a–7a, respectively) of the terminal phenyl ring reduced the ability of these compounds to inhibit COX-2 activity. In contrast, a certain degree of bulkiness and hydrophobicity in the substituted phenyl ring was highly desirable for apoptosis-inducing activity. For example, compound 2a, in which the 4-methyl moiety of celecoxib was replaced by a hydrogen atom, was a highly potent COX-2 inhibitor ($IC_{50}$=32 nM) but lacked apoptosis-inducing activity ($T_{1/2}$>100 h). Conversely, compounds 6a and 7a had no COX-2 inhibitory activity ($IC_{50}$>100 μM) but were highly potent mediators of apoptotic death in PC-3 cells ($T_{1/2}$<2 h). The time- and dose-dependent effect of compound 7a on cell viability is shown in FIG. 6A. Exposure of cells to 50 μM compound 7a resulted in a 50% decrease in cell viability within an hour, compared with 2 hours for celecoxib. Characteristics of apoptotic death in PC-3 cells are shown in FIGS. 6B–D. FIG. 6B shows pronounced changes in morphology and membrane compositions after treatment with compound 7a. As shown by phase-contrast microscopy, treated cells shrunken, rounded, and detached from the dish, and bleb formation was evident 1 hour after compound 7a was added (left panel). Morphologic evidence of apoptosis was assessed as nuclear fragmentation detected by staining cells with DAPI, and cells treated with compound 7a were found to have condensed and fragmented nuclei (center panel). Another test for apoptosis induced by compound 7a was the externalization of phosphatidylserine as detected by FITC-conjugated annexin V and fluorescence microscopy (right panel). Among other parameters, degradation of DNA to nucleosomal fragments and cleavage of PARP to the apoptosis-specific 85-kDa fragment are also well characterized events of apoptotic cell death. Results of these tests are shown in FIGS. 6C and D, respectively.

Figure 7:
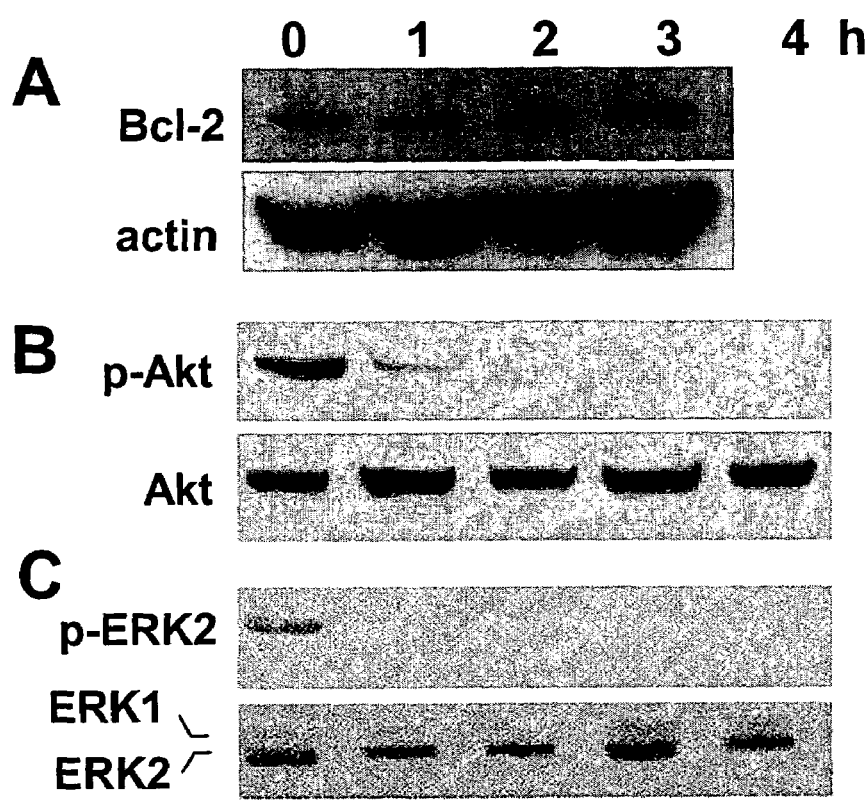
FIG. 7A shows the time-dependent effect of compound 7a on Bcl-2 expression levels, FIG. 7B the phosphorylation status of Akt, and FIG. 7C the phosphorylation status of ERK2 in PC-3 cells.

Moreover, it is noteworthy that the mechanism used by compounds 1a and 4a–7a to facilitate apoptosis through concurrent dephosphorylation of Akt and ERK2 independent of Bcl-2 was the same mechanism used by the parent compound. FIGS. 7A–C illustrates the effect of compound 7a on the expression level of Bcl-2, and the phosphorylation status of Akt and ERK2, respectively, in PC-3 cells.

In addition to PC-3 cells, we also tested the effect of compounds 1a and 4a–7a on apoptosis in the androgen-responsive LNCaP ($p53^{+/+}$) and the androgen-independent DU-145 ($p53^{-/-}$) prostate cancer cell lines. Apoptosis was induced by celecoxib and compounds 1a and 4a–7a in LNCaP and DU-145 cells with susceptibility identical to that of PC-3 cells (data not shown). Thus, these data indicate that the mechanism by which these active compounds mediate apoptosis is independent of androgen status, p53 functional status, and the level of Bcl-2 expression.

Discussion Although the clinical relevance of COX-2 inhibitors in chemoprevention has been demonstrated, the antitumor mechanism used by these compounds is not well defined (11). Mechanisms involving different signaling targets have been proposed to account for nonsteroidal anti-inflammatory drug-induced apoptosis in cancer cells. These putative mechanisms include inhibition of Bcl-2 expression (1,2), accumulation of arachidonic acid (28), stimulation of ceramide production (3), dephosphorylation of Akt and ERK2 proteins (10,25), inhibition of PPARδ (peroxisome proliferator-activated receptor) (29), and interference with the nuclear factor NF-κB signaling pathway (30). It is plausible that different COX-2 inhibitors mediate apoptosis via distinct mechanisms. However, whether COX-2 inhibition plays an obligatory role in the apoptotic effect of COX-2 inhibitors is yet to be resolved. In this study, we used COX-2 depletion via antisense COX-2 cDNA and structure-activity analysis of celecoxib derivatives to address this issue.

Use of the Tet-On antisense COX-2 clones was advantageous because these clones represented syngeneic cell lines, thereby abating the concern of genetic variations among different cell lines, and displayed differential COX-2 expression that could be shut off by doxycycline treatment. We determined that the effect of COX-2 inhibitors on apoptosis was independent of the COX-2 inhibitory activity. Although both COX-2 depletion and COX-2 inhibitors inhibited $PGE_2$ production, these two treatments had very different effects on cell viability. Treatment with COX-2 inhibitors led to cell death, but COX-2 depletion did not. The sensitivity to COX-2 inhibitor-induced apoptosis was independent of the level of COX-2 expression in the antisense clones and was, in fact, unaltered from that of parental PC-3 cells.

We were able to dissociate the apoptosis-inducing activity from the COX-2 inhibitory activity via structural modification of celecoxib. This finding is reminiscent of the previous report that sulindac metabolites, sulindac sulfide and sulindac sulfone, could induce apoptosis in prostate cancer cells via a COX-independent mechanism (22). Several celecoxib derivatives, although lacking COX-2 inhibitory activity, were as potent in eliciting apoptosis in PC-3 cells as the parent compound. These compounds induce apoptosis in both hormone-responsive and hormone-nonresponsive prostate cancer cells. Furthermore, the mechanism by which these compounds and the parental compound celecoxib induce apoptosis remained the same, i.e., facilitating the dephosphorylation of Akt- and ERK2.

CYCLOOXYGENASE-2 INHIBITORS AS MOLECULAR PLATFORMS FOR DEVELOPING A NEW CLASS OF APOPTOSIS-INDUCING AGENTS

Background: We previously demonstrated that the effect of cyclooxygenase-2 (COX-2) inhibitors on apoptosis is independent of the COX-2 inhibitory activity in prostate cancer cells. This finding provides molecular underpinnings for the development of a new class of anticancer compounds whose mode of mechanism is distinctly different from that of conventional chemotherapeutic agents. Here we embark on a project using celecoxib and rofecoxib as molecular platforms to understand the structural basis by which these compounds mediate apoptosis and to optimize their apoptosis-inducing potency in prostate cancer cells. Methods: An integrated approach combining structure-activity analysis and computer modeling was used. Structural modifications of various COX-2 inhibitors were undertaken in a systematic manner to assess the role of individual functional moieties in triggering apoptosis. Additionally, in view of the large discrepancy in potency between celecoxib and rofecoxib in apoptosis induction, molecular modeling was conducted to explore the causal structural attributes. Results: Based on the structural and computer analyses, we proposed a working model depicting distinct structural features essential to eliciting apoptosis. The structural requirements for apoptosis induction are different from that of COX-2 inhibition. Among them, hydrogen bonding through the sulfamoyl moiety and negative electrostatic potentials surrounding the heterocyclic ring are especially noteworthy. This model is validated by a tenfold increase in apoptosis-inducing potency through the alteration of the rofecoxib structure to conform with that stipulated by the model. Conclusion: We are able to develop a new class of apoptosis-inducing agents based on the molecular platforms of existing COX-2 inhibitors.

Recent epidemiological and animal-model studies have suggested the clinical application of nonsteroidal anti-inflammatory drugs (NSAIDs) as chemopreventive agents, especially in colon cancer (31–39). In light of the importance of COX-2-generated biological mediators in cell proliferation (40–44), one school of thought is that NSAIDs sensitize cancer cells to apoptosis by blocking COX-2 enzyme activity, although the exact mechanism remains unclear. Nevertheless, an expanding body of evidence suggests that COX-2 inhibition does not play a major role in NSAID-mediated apoptotic cell death (45). For example, it was reported that that metabolites of sulindac, sulindac sulfide and sulindac sulfone, were able to mediate apoptosis in cancer cells via a COX-independent mechanism (46–48). More recently, by developing Tet-On™ antisense COX-2 clones, we demonstrated that the sensitivity of prostate cancer cells to COX-2 inhibitor-induced apoptosis was independent of the COX-2 expression status (*J. Natl. Cancer Inst.*, in press). From a clinical perspective, the separation of these two pharmacological effects has significant therapeutic implications. This finding provides molecular underpinnings for the design of a new class of anticancer compounds whose mode of action is distinctly different from that of conventional chemotherapeutic agents. Our recent studies with celecoxib indicate that it interferes with multiple signaling targets including Akt and ERK2 (extracellular signal-regulated kinase 2) in prostate cancer cells (49,50). Disruption of these signaling pathways results in loss of regulation of cellular functions that govern cell growth and survival, leading to rapid apoptotic death.

This rapid induction of apoptosis, however, is unique to celecoxib since other COX-2 inhibitors examined such as rofecoxib, NS398, and DuP697, displayed nearly two orders of magnitude lower apoptosis-inducing potencies vis-à-vis celecoxib despite having comparable COX-2 inhibitory potencies (50). We thus embarked on a project using celecoxib and rofecoxib as molecular platforms to understand the structural basis underlying this discrepancy and to optimize the apoptosis-inducing potency in prostate cancer cells. Based on the structural and computer-modeling data, we were able to delineate a working model that provides insights into structural features essential to eliciting rapid apoptotic death in prostate cancer cells. More importantly, a series of new apoptosis-inducing agents with high potency were developed. These synthetic derivatives mediate apoptotic cell death irrespective of androgen sensitivity, p53 functional status, and Bcl-2 expression levels in prostate cancer cells, and thus have potential applications in prostate cancer therapy or prevention.

Materials. Celecoxib and rofecoxib were obtained from commercial capsules by solvent extraction followed by recrystallization. NS398 was purchased from Calbiochem (San Diego, Calif.). Published procedures were used for the synthesis of the following compounds: 1b and 1b-$NH_2$ (51), 2b–29b and 40b (52), 41b (53), 43b–46b (54). The identify of these known compounds was confirmed by $^1$H NMR and mass spectral analysis. Rabbit polyclonal antibodies against Akt, phospho-$^{473}$Ser Akt, p44/42 ERKs, and phospho-p44/42 ERKs were purchased from Cell Signaling Technologies (Beverly, Mass.). Rabbit polyclonal anti-poly(ADP-ribose) polymerase (PARP) antibodies were a product of PharmMingen (San Diego, Calif.). Other chemical and biochemical reagents used were obtained from Sigma (St. Louis, Mo.).

4-[5-(4-Chlorophenyl)-3-(trifluoromethyl)-1H-pyrazol-1-yl]benzene-carboxyamide (30b). The title compound was synthesized via a two-step synthesis. Step a. The preparation of 4,4,4-trifluoro-1-(4-chlorophenyl)butane-1,3-dione was carried out as follows. To a solution of ethyl trifluoroacetate (1.08 g, 7.61 mmol) in 5 mL of methyl tert-butyl ether (MTBE) was added 25% sodium methoxide in methanol (1.8 mL) over 2 min. A solution of 4'-chloroacetophenone (1 g, 6.46 mmol) in 2 mL MTBE was added to the mixture dropwise over 5 min. After stirring for 16 h, 3 N HCl (3.4 mL) was added. The organic layer was collected, washed with brine, dried over magnesium sulfate, and concentrated to give a yellow-orange solid. Recrystallization from hexane yielded the dione (1.18 g, 86%). Step b. (4-Carbamoylphenyl)hydrazine hydrochloride (228 mg, 1.21 mmol) was added to a stirred solution of the aforementioned dione (300 mg, 1.21 mmol) in 20 mL of ethanol. The mixture was stirred under reflux for 24 h, cooled to room temperature, and concentrated to dryness. The residue was dissolved in ethyl acetate, washed with brine, dried over magnesium sulfate, and concentrated to give a light brown solid. Recrystallization from ethyl acetate and hexane gave 30b (350 mg, 80%): $^1$H NMR (CDCl$_3$) δ ☐☐☐s, 1H), 7.16 (d, J=8.5 Hz, 2H), 7.34 (d, J=8.4 Hz, 2H), 7.40 (d, J=8.4 Hz, 2H), 7.83 (d, J=8.4 Hz, 2H); HRMS calc'd for M+ 365.0535. found 365.0522. Anal. ($C_{17}H_{11}ClF_3N_3O$) C, H, N.

4-[5-(2,4-Dichlorophenyl)-3-(trifluoromethyl)-1H-pyrazol-1-yl]benzene-carboxyamide (31b). The title compound was synthesized from 2',4'-dichloroacetophenone using the two-step procedure described above in 52% overall yield. $^1$H NMR (CDCl$_3$) δ ☐☐9s, 1H), 7.29 (d, J=2.0 Hz, 1H), 7.35 (d, J=8.6 Hz, 2H), 7.45 (d, J=2.0 Hz, 1H), 7.78 (d, J=8.6 Hz, 2H). HRMS calc'd for M+ 399.0145. found 399.0138. Anal. ($C_{17}H_{10}Cl_2F_3N_3O$) C, H, N.

4-[5-(2,5-Dichlorophenyl)-3-(trifluoromethyl)-1H-pyrazol-1-yl]benzene-carboxyamide (32b). The title compound was synthesized from 2',5'-dichloroacetophenone using the two-step procedure described above in 60% overall yield. $^1$H NMR (CDCl$_3$) δ ☐☐9s, 1H), 7.37 (m, 5H), 7.80 (d, J=8.5 Hz, 2H); HRMS calc'd for M+ 399.0145. found 399.0150. Anal. ($C_{17}H_{10}Cl_2F_3N_3O$) C, H, N.

4-[5-(3,4-Dichlorophenyl)-3-(trifluoromethyl)-1H-pyrazol-1-yl]benzene-carboxyamide (33b). The title compound was synthesized from 3',4'-dichloroacetophenone using the two-step procedure described above in 55% overall yield. $^1$H NMR (DMSO-d$_6$) δ 7.37s, 1H), 7.55 (d, J=8.5 Hz, 2H), 7.66 (d, J=8.5 Hz, 2H), 7.71 (d, J=2.0 Hz, 1H), 7.95 (d, J=8.5 Hz, 2H); HRMS calc'd for M+ 399.0145. found 399.0162. Anal. ($C_{17}H_{10}Cl_2F_3N_3O$) C, H, N.

4-[5-(4-Methylphenyl)-3-(trifluoromethyl)-1H-pyrazol-1-yl]benzene-carboxyamide (34b). The title compound was synthesized from 4'-methylacetophenone using the two-step procedure described above in 65% overall yield. $^1$H NMR (CDCl$_3$) δ 2.37 (s, 3H), ☐☐4s, 1H), 7.10 (d, J=8.2 Hz, 2H), 7.15 (d, J=8.2 Hz, 2H), 7.41 (dd, J=1.8, 6.7 Hz, 2H), 7.80 (dd, J=1.8, 6.7 Hz, 2H); HRMS calc'd for M+ 345.1081. found 345.1057. Anal. ($C_{18}H_{14}F_3N_3O$) C, H, N.

4-[5-(4-Trifluoromethylphenyl)-3-(trifluoromethyl)-1H-pyrazol-1-yl]benzene-carboxyamide (35b). The title compound was synthesized from 4'-trifluoromethylacetophenone using the two-step procedure described above in 53% overall yield. $^1$H NMR (CDCl$_3$) δ 7.45s, 1H), 7.54 (d, J=8.0 Hz, 2H), 7.62 (d, J=8.0 Hz, 2H), 7.79 (d, J=8.4 Hz, 2H), 8.03 (d, J=8.4

4-[5-(4-Ethylphenyl)-3-(trifluoromethyl)-1H-pyrazol-1-yl]benzene-carboxyamide (36b). The title compound was synthesized from 4'-ethylacetophenone using the two-step procedure described above in 44% overall yield. $^1$H NMR (CDCl$_3$) δ 1.24 (t, J=7.6 Hz, 3H), 2.67 (q, J=7.6 Hz, 2H), 6.74s, 1H), 7.13 (dd, J=2.2, 6.2 Hz, 4H), 7.42 (d, J=8.5 Hz, 2H), 7.81 (d, J=8.5 Hz, 2H); HRMS calc'd for M+ 359.1238. found 359.1247. Anal. ($C_{19}H_{16}F_3N_3O$) C, H, N.

4-[5-(2,4-Dimethylphenyl)-3-(trifluoromethyl)-1H-pyrazol-1-yl]benzene-carboxyamide (37b). The title compound was synthesized from 2',4'-dimethylacetophenone using the two-step procedure described above in 62% overall yield. $^1$H NMR (CDCl$_3$) δ 1.94 (s, 3H), 2.35 (s, 3 H), ☐65s, 1H), 7.03 (bs, 1H), 7.08 (t, J=8.2 Hz, 2H), 7.35 (d, J=8.6 Hz, 2H), 7.73 (d, J=8.6 Hz, 2H); HRMS calc'd for M+ 359.1238. found 359.1240. Anal. ($C_{19}H_{16}F_3N_3O$) C, H, N.

4-[5-(2,5-Dimethylphenyl)-3-(trifluoromethyl)-1H-pyrazol-1-yl]benzene-carboxyamide (38b). The title compound was synthesized from 2',5'-dimethylacetophenone using the two-step procedure described above in 58% overall yield. $^1$H NMR (CDCl$_3$) δ 1.90 (s, 3H), 2.32 (s, 3 H), ☐65s, 1H), 7.08 (m, 3H), 7.36 (d, J=8.3 Hz, 2H), 7.73 (d, J=8.5 Hz, 2H); HRMS calc'd for M+ 359.1238. found 359.1268. Anal. ($C_{19}H_{16}F_3N_3O$) C, H, N.

4-[5-(3,5-Dimethylphenyl)-3-(trifluoromethyl)-1H-pyrazol-1-yl]benzene-carboxyamide (39b). The title compound was synthesized from 3',5'-dimethylacetophenone using the two-step procedure described above in 56% overall yield. $^1$H NMR (CDCl$_3$) δ 1.91 (s, 3H), 2.34 (s, 3 H), ☐67s, 1H), 7.08 (m, 3H), 7.36 (d, J=8.3 Hz, 2H), 7.73 (d, J=8.5 Hz, 2H); HRMS calc'd for M+ 359.1238. found 359.1257. Anal. ($C_{19}H_{16}F_3N_3O$) C, H, N.

3-(4'-methylsulfonylphenyl)-4-phenyl-2(5H)-furanone (47b). The synthesis was carried out as described in Scheme 2. Step a. A mixture of 4-(methylsulfonyl)acetophenone (5.5 g, 27.8 mmol), morpholine (2.5 mL), and sulfur (0.89 g, 27.8 mmol) was refluxed for 10 h, and poured into ice. The precipitated solid was filtered, and washed with cold ethyl acetate. The solid was added to 10% sodium hydroxide (55 mL), heated to 84° C. for 12 h, and the alkaline solution was acidified with 12 N HCl. The resulting solid was filtered, dried, and recrystallized from hexane-ethyl acetate (1:1) to give 4-methylsulfonylphenylacetic acid (white solid, 4.2 g, 52% overall yield). Step b. 2-Bromoacetophenone (1.02 g, 5.12 mmol), dissolved in acetonitrile, was added to Et$_3$N (1.74 mL), followed by 4-methylsulfonylphenylacetic acid (1 g, 4.67 mmol). After 1.5 h at room temperature, 1,8-diazabicyclo[5,4,0]undec-7-ene (1.67 mL) was added. The reaction mixture was stirred for another 1 h, and then treated with 1 N HCl (35 mL). The product was extracted with ethyl acetate, dried over sodium sulfate, and recrystallized from ethyl acetate-hexane (1:1) to give 46b (880 mg, 60% overall yield). $^1$H NMR (CDCl$_3$) δ 3.08 (s, 3H), 5.24 (s, 2H), 7.18–7.30 (m, 5H), 7.66 (dd, J=1.9, 6.7 Hz, 2H), 7.96 (dd, J=1.9, 6.7 Hz, 2H); HRMS calc'd for M+ 314.0605. found 314.0632. Anal. ($C_{17}H_{14}O_4S$) C, H.

3-(4-Sulfamoylphenyl)-4-phenyl-2(5H)-furanone (48b). The title compound was synthesized in a manner similar to that described for 47b from 4-sulfamoylphenylacetic acid and 2-bromoacetophenone in 40% yield. $^1$H NMR (DMSO-d$_6$) δ 5.43 (s, 2H), 7.36–7.45 (m, 5), 7.76 (d, J=8.5 Hz, 2H), 7.96 (d, J=8.5 Hz, 2H); HRMS calc'd for M+ 315.0557. found 315.0573. Anal. ($C_{16}H_{13}NO_4S$) C, H, N.

3-(4-sulfamoylphenyl)-4-(3',4'-dichlorophenyl)-2(5H)-furanone (49b). The title compound was synthesized in a manner similar to that described for 47b from 4-sulfamoylphenylacetic acid and 2-bromo-1-(3',4'-dichlorophenyl)acetophenone in 32% yield. $^1$H NMR (DMSO-d$_6$) δ 5.42 (s, 2H), 7.26 (dd, J=2.5, 8.5 Hz, 1H), 7.42 (bs, 1H), 7.55 (d, J=8.5 Hz, 1 H), 7.71 (d, J=8.5 Hz, 2H), 7.86 (d, J=8.5 Hz, 2H); HRMS calc'd for M+ 382.9778. found 382.9764. Anal. ($C_{16}H_{11}Cl_2NO_4S$) C, H, N.

3-(4-sulfamoylphenyl)-4-(2',4'-dichlorophenyl)-2(5H)-furanone (50b). The title compound was synthesized in a manner similar to that described for 47b from 4-sulfamoylphenylacetic acid and 2-bromo-1-(2',4'-dichlorophenyl)acetophenone in 30% yield. $^1$H NMR (DMSO-d$_6$) δ 5.42 (s, 2H), 7.26 (dd, J=2.5, 8.5 Hz, 1H), 7.42 (bs, 1H), 7.55 (d, J=8.5 Hz, 1 H), 7.71 (d, J=8.5 Hz, 2H), 7.86 (d, J=8.5 Hz, 2H); HRMS calc'd for M+ 382.9778. found 382.9785. Anal. ($Cl_6H_{11}Cl_2NO_4S$) C, H, N.

Cell culture. Human prostate cancer cell lines LNCaP and PC-3 were purchased from American Type Culture Collection (Rockville, Md.). Cells were cultured in RPMI 1640 medium supplemented with 10% fetal bovine serum (FBS) at 37° C. in a humidified 5% CO$_2$ incubator. Cells were replenished daily with a new medium and were passaged 1:4 with fresh medium every three days.

Cell viability analysis. Prostate cancer cells were grown in 10% FBS-supplemented RPMI 1640 medium for 48 h, and were exposed to various concentrations of celecoxib dissolved in DMSO (final concentration 0.1%) in serum-starved RPMI 1640 medium for different time intervals. Controls received DMSO vehicle at a concentration equal to that in celecoxib-treated cells. During the treatment, the percentage of cells floating in the medium increased over time. Adherent cells were harvested by trypsinization, and floating cells were recovered by centrifugation at 3,200×g for 5 min. Cell morphology was observed with a light microscope at 200×. Both adherent and floating cells were combined for the assessment of cell viability. Cell viability was determined by trypan blue exclusion.

Analysis for Apoptosis

Apoptosis ELISA. Induction of apoptosis was also assessed by using a "Cell Death Detection ELISA" assay (Boehringer-Mannheim) following the manufacturer's instructions. This test is based on the quantitative determination of cytoplasmic histone-associated DNA fragments in the form of mono- and oligonucleosomes after induced apoptotic death. In brief, PC-3 cells ($2.5 \times 10^6$) were plated on a T-75 flask 24 h before experiment. Cells were washed by 5 mL of serum-free RPMI 1640 medium twice, and were then treated with the test agent at different concentrations or DMSO vehicles for different time intervals. Both floating and adherent cells were collected, and cell lysates equivalent to $10^4$ cells were used for the ELISA analysis.

Western blot analysis of cleavage. Drug-treated cells were collected, washed with ice-cold PBS, and resuspended in Lysis Buffer consisting of 20 mM Tris-HCl, pH 8, 137 mM NaCl, 1 mM $CaCl_2$, 10% glycerol, 1% Nonidet P-40, 0.5% deoxycholate, 0.1% sodium dodecylsulfate, 100 µM 4-(2-aminoethyl)benzenesulfonyl fluoride, 10 µg/mL leupeptin, and 10 µg/mL aprotinin. Soluble cell lysates were collected after centrifugation at 1,500×g for 5 min. Equivalent protein concentrations were resolved in 10% SDS-polyacrylamide gels, and were transferred to nitrocellulose membranes. Immunoblotting with anti-PARP antibodies was carried out as described above.

Immunoblotting. The general procedure for the Western blot analysis of Akt, phospho-Akt, ERKs, and phospho-ERKs is described as follows. Cells were washed in PBS, resuspended in SDS gel-loading buffer, sonicated by an ultrasonic sonicator for 5 sec, and boiled for 5 min. After brief centrifugation, equivalent protein concentrations from the soluble fractions were resolved in 10% SDS-polyacrylamide gels on a Minigel apparatus, and transferred to a nitrocellulose membrane using a semi-dry transfer cell. The transblotted membrane was washed twice with TBS containing 0.05% Tween 20 (TBST). After blocking with TBS containing 5% nonfat milk for 60 min, the membrane was incubated with the primary antibody with 1:1,000 dilution in TBS-1% low fat milk at 4° C. for 12 h, and washed twice with TBST. The membrane was probed with goat anti-rabbit IgG-HRP conjugates (1:5,000) for 1 h at room temperature and washed twice with TBST. The immunoblots were visualized by enhanced chemiluminescence.

Figure 11:
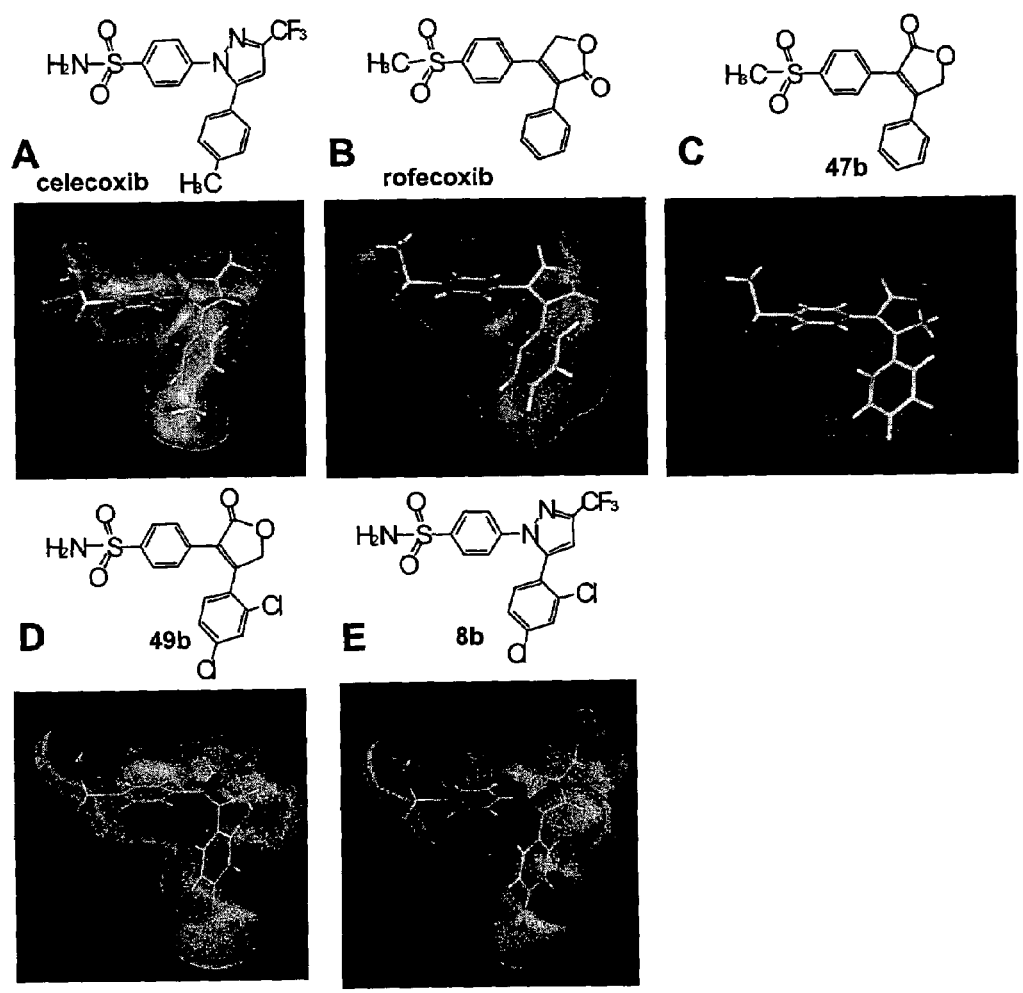
FIG. 11 shows computer modeling of celecoxib, rofecoxib, compound 47b, compound 49b, and compound 8b.

Molecular Modeling Experiments. Each of the compounds celecoxib, rofecoxib and 47b (FIG. 11), was initially subjected to 1000 steps of Monte-Carlo (MC) simulation using the Merck Molecular Force Field (MMFF) available in Macromodel7.0 (55). The minimum conformation reached by the MC simulations was then fully optimized at the Density Functional Theory (DFT) level of B3LYP/6-31G* with Gaussian 98A7 in the gas phase (56). All the three minimum energy structures were confirmed by normal mode analysis with no negative frequency found. Computations for the electrostatic potential (EP) and electron density were then carried out for each of the fully optimized structures with a grid of 216,000 points using Gaussian 98A7. The pictures of Electrostatic Potential maps for each compound were generated by gOpenMol (57,58) with the electrostatic potential mapped onto the electron density. The isosurface value is 0.0004 with a range for the EP of −0.03 to 0.03.

Statistical analysis. Each experiment was performed in triplicate, and was repeated at least two times on different occasions.

Results

Strategy A: the terminal aromatic ring was modified with various substituents (compounds 2b–23b, Table 2), or was replaced by different ring systems (24b–29b, Table 2).

Figure 10:
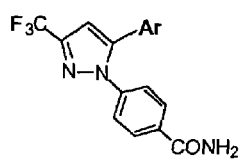
FIG. 10A is a table showing the potency of compounds 30b–39b.
FIG. 10B shows the time course of formation of nucleosomal DNA in PC-3 cells treated with DMSO or compound 37b, and a Western blot showing induction of PARP cleavage by compound 37b.
FIG. 10C is a Western blot showing the time-dependent effect of compound 37 on Akt and ERK-2 phosphorylation.
Figure 10:
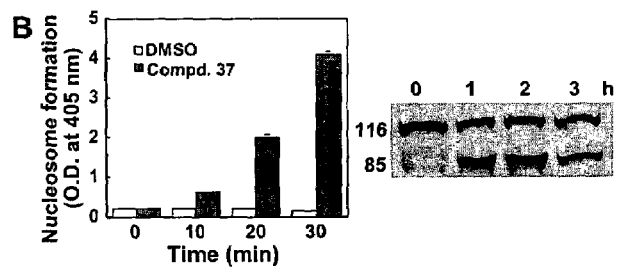
Figure 10:
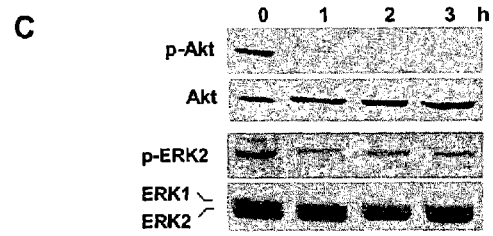

Strategy B: although both the sulfonamide and methylsulfone pharmacophores showed comparable potency in COX-2 inhibition (52), the apoptosis-inducing activity was abrogated when the sulfamoyl moiety of celecoxib was replaced by a methylsulfonyl group. We further investigated whether the carboxamide group was a suitable bioisostere for the sulfonamide in a series of celecoxib analogues (30b–39b, FIG. 10).

Strategy C: we prepared compounds 40b–46b to assess the effect of the heterocyclic system in modulating apoptosis-inducing potency. Computer modeling analysis of celecoxib versus rofecoxib suggests a correlation between the surface electrostatic potential surrounding the heterocyclic system and the apoptosis-inducing potency. A final, more comprehensive strategy was to compare vis-à-vis the entire molecules of active celecoxib and inactive rofecoxib in terms of their surface electrostatic potential (vide infra). Since this comparison revealed important differences in electron density, an effort to modify the molecule of rofecoxib to approximate the surface electrostatic potential of celecoxib resulted in the design of structural variants 47b–50b.

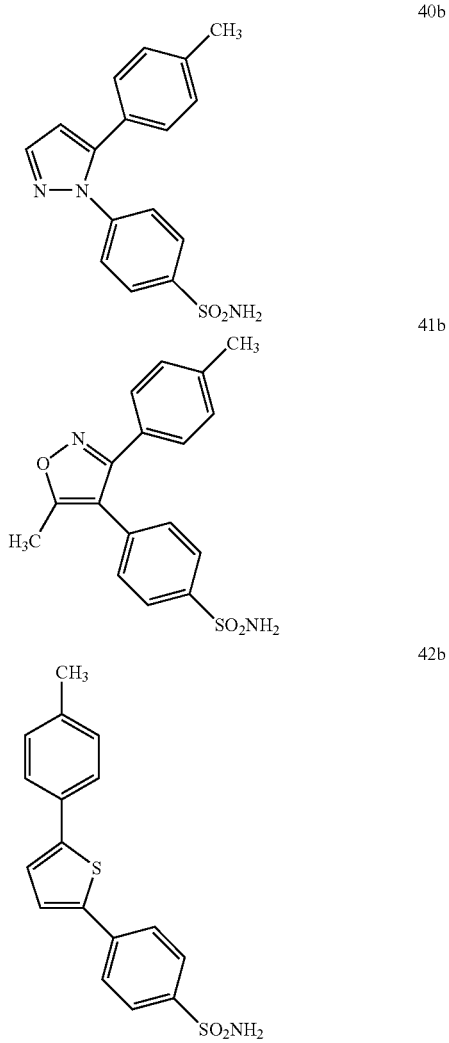

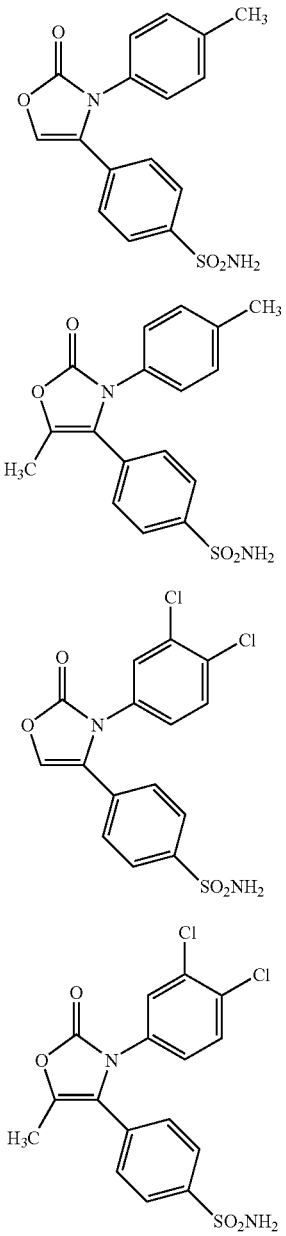

Figure 8:
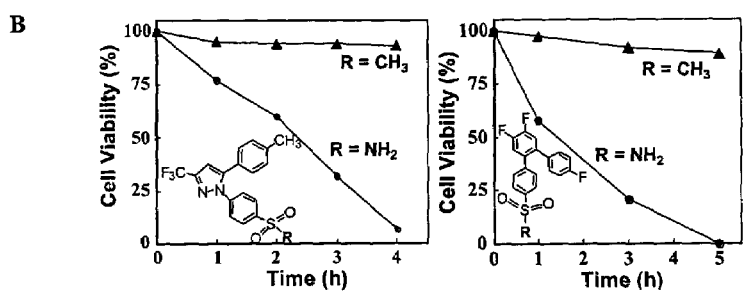
FIG. 8A shows the structures, IC50 in COX-2 inhibition, and the apoptosis-inducing potency ($T_{1/2}$) of various COX-2 inhibitors.
FIG. 8B shows a comparison of the effect of sulfonamide versus methylsulfone on cell viability.

The sulfamoyl moiety plays a pivotal role in the effect of celecoxib on apoptosis. Different COX-2 inhibitors with similar IC$_{50}$ values in COX-2 inhibition exhibit a wide discrepancy in apoptosis-inducing potency in prostate cancer cells. Accordingly, COX-2 inhibitors could be classified into fast-acting and slow-acting apoptosis inducers (FIG. 8). Representatives of the slow-acting apoptosis inducer included rofecoxib, NS398, DuP697, and the terphenyl derivative 1b. This discrepancy underscores differences in the biochemical mechanisms underlying the apoptotic action of these COX-2 inhibitors. As shown in FIG. 8, there exists an apparent structural difference between celecoxib and the slow-acting apoptosis-inducing COX-2 inhibitors, i.e., sulfonamide versus methylsulfone. This distinct difference suggests that the sulfamoyl moiety plays a role in the high potency of celecoxib in inducing apoptosis. This premise is corroborated by the loss of high potency following the conversion of celecoxib to its methylsulfone counterpart (FIG. 8B, left panel). Moreover, transformation of compound 1b to 1b-NH$_2$ (51) resulted in an increase in apoptosis-inducing activity by an order of magnitude (FIG. 8B, right panel). The conversion of rofecoxib and DuP697 to their sulfonamide counterparts, however, had no significant change in the respective apoptosis-inducing activities, indicating that other structural elements were involved in the activation of the apoptosis machinery.

Strategy A. A series of derivatives were synthesized to assess the effect of the terminal phenyl ring on the apoptosis-inducing potency (Table 2), many of which were also potent COX-2 inhibitors (52). In line with our preliminary data (*J. Natl. Cancer Inst.*, in press), there was no direct correlation between the apoptosis-inducing and COX-2 inhibitory activities, confirming that these two pharmacological activities could be separated.

TABLE 2

Apoptosis induction and COX-2 inhibition data for celecoxib and 2b–29b.

| Compound | Ar | T½ (h) 50 μM | IC$_{50}$ (μM) |
|---|---|---|---|
| celecoxib | Cl, Cl (with Cl) | 2 | 0.040 |
| 2b | Cl, Cl (with Cl) | >100 | 0.032 |
| 3b | —⟨phenyl⟩—F | >100 | 0.041 |
| 4b | F, —⟨phenyl⟩—F | >100 | N.D. |

All compounds described herein were evaluated for their ability to induce apoptotic death in three separate cell lines, including androgen-dependent LNCaP (p53+/+), androgen-independent PC-3 (p53−/−), and Bcl-2-overexpressing PC-3 (PC-3/Bcl-2) (49). The potency of individual compounds was expressed as T$_{1/2}$ that denotes the time required for eliciting 50% apoptotic death at the indicated concentration. Results obtained with these cell lines were virtually identical, indicating that the induction of apoptosis was independent of androgen sensitivity, p53 functional status, and Bcl-2 expressing levels. Selected compounds were evaluated for the effect on the phosphorylation status of Akt and ERK2, which has been correlated with celecoxib-induced apoptotic death (49,50).

TABLE 2-continued

Apoptosis induction and COX-2 inhibition data for celecoxib and 2b–29b.

| Compound | Ar | T½ (h) 50 µM | IC50 (µM) |
|---|---|---|---|
| 5b | 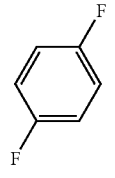 2,5-difluorophenyl | >100 | N.D. |
| 6b | 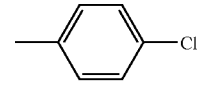 4-Cl-phenyl | 3 | 0.056 |
| 7b | 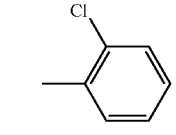 2-Cl-phenyl | 4 | 0.01 |
| 8b | 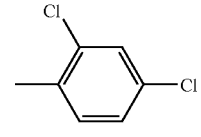 2,4-diCl-phenyl | 2 | 0.056 |
| 9b | 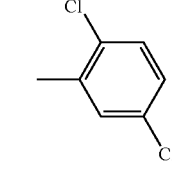 2,5-diCl-phenyl | 3 | >100 |
| 10b | 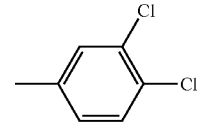 3,4-diCl-phenyl | 1.5 | 0.015 |
| 11 |  4-OH-phenyl | >100 | >100 |
| 12b | 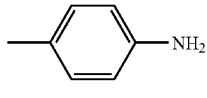 4-NH2-phenyl | >100 | 0.34 |
| 13b | 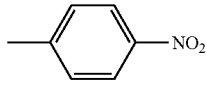 4-NO2-phenyl | >100 | 2.63 |
| 14b | 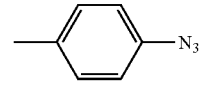 4-N3-phenyl | 1.5 | N.D. |
| 15b | 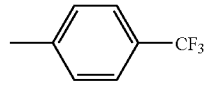 4-CF3-phenyl | 3 | 8.23 |
| 16b | 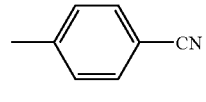 4-CN-phenyl | >100 | N.D. |
| 17b | 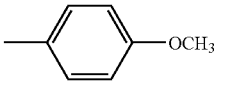 4-OCH3-phenyl | >100 | 0.008 |
| 18b | 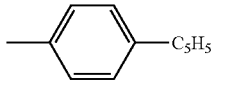 4-C5H5-phenyl | 2.5 | 0.86 |
| 19b | 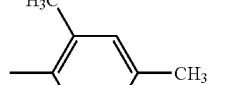 2,4-diCH3-phenyl | 2 | 0.12 |
| 20b |  2,4-diCH3-phenyl | 1.5 | >100 |
| 21b | 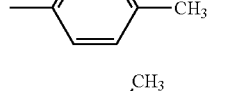 2,4-diCH3-phenyl | 2 | N.D. |
| 22b | 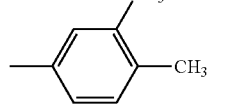 2,4-diOCH3-phenyl | >100 | N.D. |
| 23b | 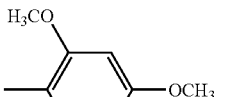 2,4-diOCH3-phenyl | >100 | N.D. |
| 24b | 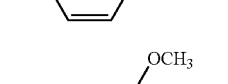 2-pyridyl | >100 | 45.6 |
| 25b | 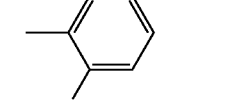 cyclohexenyl | >100 | 0.084 |
| 26b | 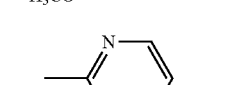 2-furyl | >100 | N.D. |
| 27b | 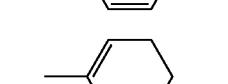 2-thienyl | >100 | N.D. |
| 28b | 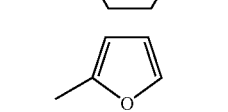 5-Cl-2-thienyl | >100 | 0.025 |

TABLE 2-continued

Apoptosis induction and COX-2 inhibition data for celecoxib and 2b–29b.

| Compound | Ar | T½ (h) 50 μM | IC$_{50}$ (μM) |
|---|---|---|---|
| 29b | 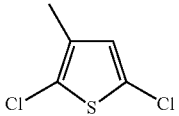 | >100 | N.D. |

Figure 9:
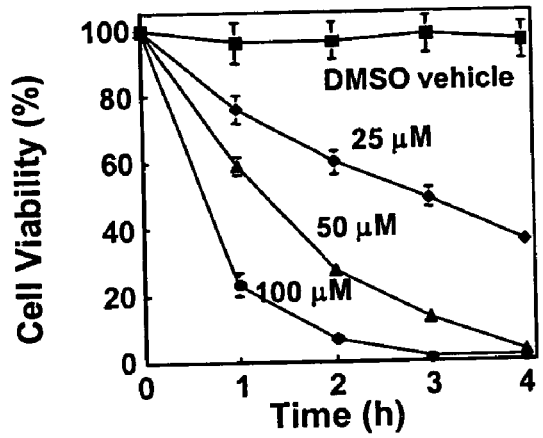
FIG. 9A shows the time- and dose-dependent effect of compound 10b on the cell viability of PC-3 cells in serum-starved RPMI 1640 medium.
FIG. 9B (left) shows the time course of the formation of nucleosomal DNA in PC-3 cells treated with DMSO vehicles or compound 10(b) (50 μM), as measured by Cell Death Detection ELISA.
FIG. 9C shows the time-dependent effect of 50 μM compound 10b on Akt and ERK-2 phosphorylation. Phosphorylation status was determined by immunoblotting with the respective phospho-specific antibodies.
Figure 9:
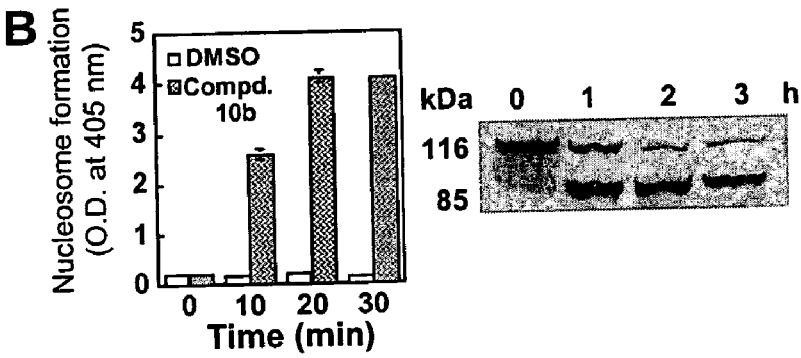
Figure 9:
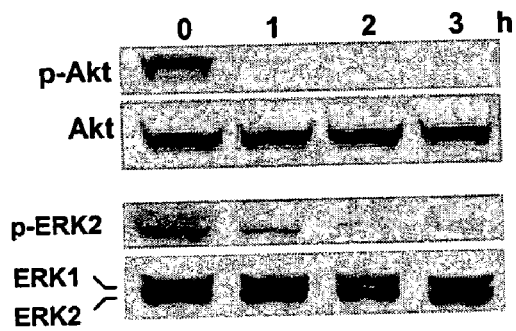

While some compounds displayed high potency in inducing apoptosis, they lacked significant COX-2 inhibitory activity, and vice versa. With regard to structure requirements for apoptosis induction, a certain degree of bulkiness and hydrophobicity in the 5-aryl ring was desirable, which was distinct from that of COX-2 inhibition. Reducing the size (i.e., CH$_3$→H or F) or increasing the polarity (CH$_3$→OH, NH$_2$, or NO$_2$) precipitously attenuated the activity. Among the twenty-eight derivatives examined, compounds 10b, 14b, and 20b exhibited the highest potency in triggering cell death in PC-3 cells (T$_{1/2}$ at 50 μM, 1.5 h), followed by compounds 6b–9b, 15b, 19b, and 21b (T$_{1/2}$ at 50 μM, 2 to 4 h), while the rest displayed poor potency (>100 h). It is noteworthy that the mechanism by which these active compounds facilitated apoptosis remained unaltered vis-à-vis celecoxib, i.e., concomitant dephosphorylation of Akt and ERK2. FIG. 9 depicts the time-and/or dose-dependent effect of compound 10b on cell viability (panel A), evidence for the apoptotic death (panel B), and the phosphorylation status of Akt and ERK2 (panel C) in PC-3 cells, which is reminiscent to that observed with celecoxib (49, 50).

Strategy B. The disparity in apoptosis-inducing activity between the sulfonamide and methylsulfone compounds suggests that the former pharmacophore confers optimal potency in apoptosis induction. We further investigated whether this functional group could be replaced by a carboxamide moiety without abrogating activity. Accordingly, we investigated compounds 30b–39b (FIG. 10A) that possessed a carboxamide group in place of the sulfonamide present in celecoxib and in compounds 6b, 8b–10b, 15b, and 18b–21b. As shown in FIG. 10A, replacement of —SO$_2$NH$_2$ with —CONH$_2$ in 8b→31b, 9b→32b, 10b→33b, and 19b→37b had no appreciable change in the potency in apoptosis induction. However, for the rest of the compounds examined, the replacement resulted in a significant reduction in activity. This observation suggests that the modes of interaction of these two pharmacophores with the target protein(s) differed. However, this structural modification did not alter the mechanism by which these carboxamides mediated apoptosis, i.e., by facilitating Akt and ERK2 dephosphorylation. With compound 37b as an example, FIGS. 10B and C illustrate the evidence of apoptotic death and the time-dependent effect on Akt and ERK, respectively.

Strategy C. As mentioned before, the sulfonamide counterparts of rofecoxib and DuP697 showed poor activities in apoptosis induction. In addition, we examined the effect of a number of benzenesulfonamides with different heterocyclic rings (40b–45b) on the cell viability of PC-3 cells. Despite the presence of the sulfonamide group, all of these compounds displayed low potency in apoptosis induction (T$_{1/2}$ at 50 μM, >100 h). Even a slight modification of the pyrazole ring of celecoxib such as the removal of the trifluoromethyl moiety (compound 40b) resulted in the loss of high potency. These data prompted a notion that the heterocyclic ring played a necessary role in interacting with the signaling target(s) responsible for apoptosis. Accordingly, we conducted a molecular modeling analysis of the two prototypic drugs, celecoxib and rofecoxib, to examine the respective electrostatic potential surrounding the heterocyclic system (FIGS. 11A and B). The electron density of individual areas is coded in colors, in which blue and red denote negative and positive electrostatic potentials, respectively. Changes in between are seen in transition from blue to red. As shown, distinct differences were noted between pyrazole and lactone rings which appear to have opposite electron density profiles as the red and blue colors indicate. This finding suggests that the heterocyclic ring in rofecoxib is more electropositive than that of celecoxib.

Based on these computer modeling data, we set out to alter the surface potential of rofecoxib to mimic with that of celecoxib by repositioning the lactone carbonyl in the opposite orientation (FIG. 11C). In making this change, the total electron density map of the resulting isomer 47b was similar to that of celecoxib (A vs. C). However, since the methylsulfone 47b showed poor activity in eliciting apoptosis in PC-3 cells, we turned our attention to the corresponding sulfonamide counterpart 48b and its dichloro-analogues 49b and 50b.

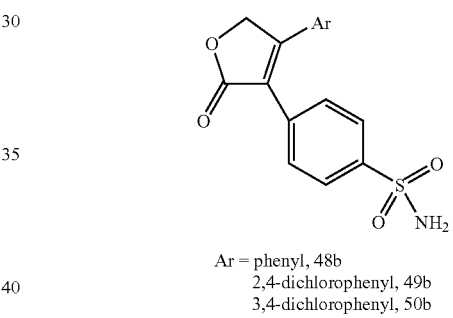

Ar = phenyl, 48b
2,4-dichlorophenyl, 49b
3,4-dichlorophenyl, 50b

Among them, compound 49b was most noteworthy since its activity in apoptosis induction increased significantly (T$_{1/2}$ at 50 μM, 15 h) vis-à-vis rofecoxib, 48b, and 50b (T$_{1/2}$ at 100 μM, >100 h). It is noteworthy that the electrostatic potential map of compound 49b exhibited a high degree of resemblance to its pyrazole counterpart 8b (T$_{1/2}$ at 50 μM, 2 h), and that the electron density correlation between 49b and 8b (FIGS. 11D & E) was akin to that between celecoxib and 47b, but improved on the 5-aryl moiety.

These data demonstrate that a clear understanding of the stereoelectronic effects of the entire conjugated system may represent a novel way of correlating structural changes with apoptosis-inducing activity.

Figure 12:
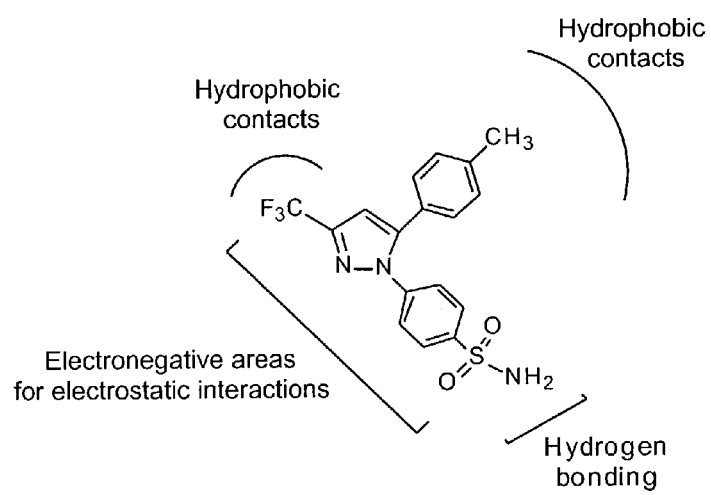
FIG. 12 is a working model depicting the interaction between celecoxib and its protein target.

In this study, we embarked on a project to optimize apoptosis-inducing activity and potency via structural modifications based on the molecular platforms of celecoxib and rofecoxib. According to the structure-activity data, we propose a working model as shown in FIG. 12 to account for the interaction between celecoxib and its protein target that triggers apoptosis in prostate cancer cells.

There exist stringent structural requirements with regard to the amide moiety and the heterocyclic system in the induction of apoptotic death in PC-3 cells. In contrast, the terminal phenyl ring displays a high degree of tolerance in structural alterations. Our data show that the apoptosis-inducing potency could be enhanced by replacing the methyl function with a variety of apolar substituents. However, reduction in the size or increase in the hydrophilicity of these substituents would precipitously attenuate the activity.

In summary, the impetus of the present study is multifold. First, from a clinical perspective, the separation of the COX-2 inhibitory activity from the apoptosis-inducing effect provides a molecular basis for the design of a new class of apoptosis-inducing agents. Second, in addition to PC-3 cells, these molecules are equally effective in androgen-dependent LNCaP prostate cancer cells and Bcl-2-overexpressing PC-3 cells (data not shown). This observation indicates that the induction of apoptosis by these novel agents is independent of androgen sensitivity and genetic abnormalities associated with advanced prostate cancer. Together, these apoptosis-inducing agents represent potential candidates for the chemoprevention or therapy of human prostate cancer.

All documents referenced herein are incorporated by reference.

Although this invention has been described with respect to specific embodiments, the details of these embodiments are not to be construed as limitations.

REFERENCES (1) Sheng H, Shao J, Morrow J D, Beauchamp R D, DuBois R N: Modulation of apoptosis and Bcl-2 expression by prostaglandin $E_2$ in human colon cancer cells. Cancer Res 1998; 58:362–6.
(2) Liu X H, Yao S, Kirschenbaum A, Levine A C: NS398, a selective cyclooxygenase-2 inhibitor, induces apoptosis and down-regulates bcl-2 expression in LNCaP cells. Cancer Res 1998;58:4245–9.
(3) Chan T A, Morin P J, Vogelstein B, Kinzler K W: Mechanisms underlying nonsteroidal antiinflammatory drug-mediated apoptosis. Proc Natl Acad Sci USA 1998; 95:681–6.
(4) Piazza G A, Rahm A L, Krutzsch M, Sperl G, Paranka N S, Gross P H, et al: Antineoplastic drugs sulindac sulfide and sulfone inhibit cell growth by inducing apoptosis. Cancer Res 1995; 55:3110–6.
(5) Hanif R, Pittas A, Feng Y, Koutsos M I, Qiao L, Staiano-Coico L, et al: Effects of nonsteroidal anti-inflammatory drugs on proliferation and on induction of apoptosis in colon cancer cells by a prostaglandin-independent pathway. Biochem Pharmacol 1996; 52:237–45.
(6) Thompson H J, Jiang C, Lu J, Mehta R G, Piazza G A, Paranka N S, et al: Sulfone metabolite of sulindac inhibits mammary carcinogenesis. Cancer Res 1997; 57:267–71.
(7) Jones M K, Wang H, Peskar B M, Levin E, Itani R M, Sarfeh I J, et al: Inhibition of angiogenesis by nonsteroidal anti-inflammatory drugs: insight into mechanisms and implications for cancer growth and ulcer healing. Nat Med 1999; 5:1418–23.
(8) Williams C S, Tsujii M, Reese J, Dey S K, DuBois R N: Host cyclooxygenase-2 modulates carcinoma growth. J Clin Invest 2000; 105:1589–94.
(9) Zhang X, Morham S G, Langenbach R, Young D A: Malignant transformation and antineoplastic actions of nonsteroidal antiinflammatory drugs (NSAIDs) on cyclooxygenase-null embryo fibroblasts. J Exp Med 1999; 190:451–59.
(10) Hsu A L, Ching T T, Wang D S, Song X, Rangnekar V M, Chen C S: The cyclooxygenase-2 inhibitor celecoxib induces apoptosis by blocking Akt activation in human prostate cancer cells independently of Bcl-2. J Biol Chem 2000; 275:11397–403.
(11) Marx J: Cancer research. Anti-inflammatories inhibit cancer growth—but how? Science 2001; 291:581–2.
(12) Hla T, Ristimaki A, Appleby S, Barriocanal J G: Cyclooxygenase gene expression in inflammation and angiogenesis. Ann NY Acad Sci 1993; 696:197–204.
(13) Dubois R N, Abramson S B, Crofford L, Gupta R A, Simon L S, Van De Putte L B, et al: Cyclooxygenase in biology and disease. Faseb J 1998; 12:1063–73.
(14) Taketo M M: Cyclooxygenase-2 inhibitors in tumorigenesis (part I). J Natl Cancer Inst 1998;90:1529–36.
(15) Hla T, Bishop-Bailey D, Liu C H, Schaefers H J, Trifan O C: Cyclooxygenase-1 and -2 isoenzymes. Int J Biochem Cell Biol 1999;31:551–7.
(16) Prescott S M, Fitzpatrick F A: Cyclooxygenase-2 and carcinogenesis. Biochim Biophys Acta 2000; 1470: M69–78.
(17) Tsujii M, DuBois R N: Alterations in cellular adhesion and apoptosis in epithelial cells overexpressing prostaglandin endoperoxide synthase 2. Cell 1995; 83:493–501.
(18) DuBois R N, Shao J, Tsujii M, Sheng H, Beauchamp R D: G1 delay in cells overexpressing prostaglandin endoperoxide synthase-2. Cancer Res 1996; 56:733–7.
(19) McGinty A, Chang Y W, Sorokin A, Bokemeyer D, Dunn M J: Cyclooxygenase-2 expression inhibits trophic withdrawal apoptosis in nerve growth factor-differentiated PC12 cells. J Biol Chem 2000; 275:12095–101.
(20) Oshima M, Dinchuk J E, Kargman S L, Oshima H, Hancock B, Kwong E, et al: Suppression of intestinal polyposis in Ape delta716 knockout mice by inhibition of cyclooxygenase 2 (COX-2). Cell 1996;87:803–9.
(21) Liu C H, Chang S H, Narko K, Trifan O C, Wu M T, Smith E, et al: Overexpression of cyclooxygenase-2 is sufficient to induce tumorigenesis in transgenic mice. J Biol Chem 2001; 276:18563–9.
(22) Lim J T, Piazza G A, Han E K, Delohery T M, Li H, Finn T S, et al: Sulindac derivatives inhibit growth and induce apoptosis in human prostate cancer cell lines. Biochem Pharmacol 1999; 58:1097–107.
(23) Narko K, Ristimaki A, MacPhee M, Smith E, Haudenschild C C, Hla T: Tumorigenic transformation of immortalized ECV endothelial cells by cyclooxygenase-1 overexpression. J Biol Chem 1997; 272:21455–60.
(24) Trifan O C, Smith R M, Thompson B D, Hla T: Overexpression of cyclooxygenase-2 induces cell cycle arrest. Evidence for a prostaglandin-independent mechanism. J Biol Chem 1999; 274:34141–7.
(25) Johnson A J, song X, Hsu A, Chen C: Apoptosis signaling pathways mediated by cyclooxygenase-2 inhibitors in prostate cancer cells. Adv Enzyme Regul 2001; 41:221–35.
(26) Chinery R, Coffey R J, Graves-Deal R, Kirkland S C, Sanchez S C, Zackert W E, et al: Prostaglandin J2 and 15-deoxy-delta12,14-prostaglandin J2 induce proliferation of cyclooxygenase-depleted colorectal cancer cells. Cancer Res 1999; 59:2739–46.
(27) Penning T D, Talley J J, Bertenshaw S R, Carter J S, Collins P W, Docter S, et al: Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benzenesulfonamide (SC-58635, celecoxib). J Med Chem 1997; 40:1347–65.

(28) Cao Y, Pearman A T, Zimmerman G A, McIntyre T M, Prescott S M: Intracellular unesterified arachidonic acid signals apoptosis. Proc Natl Acad Sci USA 2000; 97:11280–5.

(29) He T C, Chan T A, Vogelstein B, Kinzler K W: PPARdelta is an APC-regulated target of nonsteroidal anti-inflammatory drugs. Cell 1999; 99:335–45.

(30) Yin M J, Yamamoto Y, Gaynor R B: The anti-inflammatory agents aspirin and salicylate inhibit the activity of I(kappa)B kinase-beta. Nature 1998; 396:77–80.

(31) Peleg, I I, Wilcox C M: The Role of Eicosanoids, Cyclooxygenases, and Nonsteroidal Anti-inflammatory Drugs in Colorectal Tumorigenesis and Chemoprevention. J Clin Gastroenterol 2002; 34:117–25.

(32) Krishnan K, Brenner D E: Prostaglandin inhibitors and the chemoprevention of noncolonic malignancy. Gastroenterol Clin North Am 2001; 30:981–1000.

(33) Vainio H: Is COX-2 inhibition a panacea for cancer prevention? Int J Cancer 2001; 94:613–4.

(34) Sjodahl R: Extent, mode, and dose dependence of anticancer effects. Am J Med 2001; 110:S66–S69.

(35) Lynch P M: COX-2 inhibition in clinical cancer prevention. Oncology (Huntingt) 2001; 15:21–6.

(36) Castelao J E, Yuan J M, Gago-Dominguez M, Yu M C, Ross R K: Non-steroidal anti-inflammatory drugs and bladder cancer prevention. Br J Cancer 2000; 82:1364–9.

(37) Harris R E, Alshafie G A, Abou-Issa H, Seibert K: Chemoprevention of breast cancer in rats by celecoxib, a cyclooxygenase 2 inhibitor. Cancer Res 2000; 60:2101–3.

(38) Fournier D B, Gordon G B: COX-2 and colon cancer: Potential targets for chemoprevention. J Cell Biochem 2000; 77:97–102.

(39) Nelson J E, Harris R E: Inverse association of prostate cancer and non-steroidal anti-inflammatory drugs (NSAIDs): results of a case-control study. Oncol Rep 2000; 7:169–70.

(40) Hla T, Ristimaki A, Appleby S, Barriocanal J G: Cyclooxygenase gene expression in inflammation and angiogenesis. Ann NY Acad Sci 1993; 696:197–204.

(41) Taketo M M: Cyclooxygenase-2 inhibitors in tumorigenesis (part I). J Natl Cancer Inst 1998; 90: 1529–36.

(42) Dubois R N, Abramson S B, Crofford L, Gupta R A, Simon L S, Van De Putte L B, et al: Cyclooxygenase in biology and disease. Faseb J 1998; 12:1063–73.

(43) Hla T, Bishop-Bailey D, Liu C H, Schaefers H J, Trifan O C: Cyclooxygenase-1 and -2 isoenzymes. Int J Biochem Cell Biol 1999; 31:551–7.

(44) Williams C S, Mann M, DuBois R N: The role of cyclooxygenases in inflammation, cancer, and development. Oncogene 1999; 18:7908–16.

(45) Marx J: Cancer research. Anti-inflammatories inhibit cancer growth—but how? Science 2001; 291:581–2.

(46) Piazza G A, Rahm A L, Krutzsch M, Sperl G, Paranka N S, Gross P H, et al: Antineoplastic drugs sulindac sulfide and sulfone inhibit cell growth by inducing apoptosis. Cancer Res 1995; 55:3110–6.

(47) Lim J T, Piazza G A, Han E K, Delohery T M, Li H, Finn T S, et al: Sulindac derivatives inhibit growth and induce apoptosis in human prostate cancer cell lines. Biochem Pharmacol 1999; 58:1097–107.

(48) Thompson H J, Jiang C, Lu J, Mehta R G, Piazza G A, Paranka N S, et al: Sulfone metabolite of sulindac inhibits mammary carcinogenesis. Cancer Res 1997; 57:267–71.

(49) Hsu A L, Ching T T, Wang D S, Song X, Rangnekar V M, Chen C S: The cyclooxygenase-2 inhibitor celecoxib induces apoptosis by blocking Akt activation in human prostate cancer cells independently of Bcl-2. J Biol Chem 2000; 275:11397–403.

(50) Johnson A J, song X, Hsu A, Chen C: Apoptosis signaling pathways mediated by cyclooxygenase-2 inhibitors in prostate cancer cells. Adv Enzyme Regul 2001; 41:221–35.

(51) Li J J, Norton M B, Reinhard E J, Anderson G D, Gregory S A, Isakson P C, et al: Novel terphenyls as selective cyclooxygenase-2 inhibitors and orally active anti-inflammatory agents. J Med Chem 1996; 39:1846–56.

(52) Penning T D, Talley J J, Bertenshaw S R, Carter J S, Collins P W, Docter S, et al: Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benzenesulfonamide (SC-58635, celecoxib). J Med Chem 1997; 40:1347–65.

(53) Talley J J, Brown D L, Carter J S, Graneto M J, Koboldt C M, Masferrer J L, et al: 4-[5-Methyl-3-phenylisoxazol-4-yl]-benzenesulfonamide, valdecoxib: a potent and selective inhibitor of COX-2. J Med Chem 2000; 43:775–7.

(54) Puig C, Crespo M I, Godessart N, Feixas J, Ibarzo J, Jimenez J M, et al: Synthesis and biological evaluation of 3,4-diaryloxazolones: A new class of orally active cyclooxygenase-2 inhibitors. J Med Chem 2000; 43:214–23.

(55) Schrödinger I. Portland, Oreg. http://www.schrödinger.com.

(56) Frisch M J, Trucks G W, Schlegel H B, Scuseria G E, Robb M A, Cheeseman J R, et al: Gaussian 98 (Revision A7). Pittsburg, Pa.: Gaussian Inc.; 1998.

(57) Laaksonen L: A graphics program for the analysis and display of molecular dynamics trajectories. J Mol Graphics 1992; 10:33–34.

(58) Bergman D L, Laaksonen L, Laaksonen A: Visualization of Solvation Structures in Liquid Mixtures. J. Mol. Graphics & Modelling 1997; 15:301–06.

The invention claimed is:

1. A compound of formula I:

wherein
$R^1$ is carboxyamide;
$R^2$ is selected from the group consisting of alkyl and haloalkyl; and
Ar is an aryl radical selected from phenyl, biphenyl, naphthyl, anthryl, phenanthrenyl, and fluorenyl; and wherein Ar is optionally substituted with one or more radicals selected from the group consisting of halo, azido, $C_1$–$C_4$ alkyl, $C_1$–$C_4$ haloalkyl, $C_1$–$C_4$ azidoalkyl, aryl, alkylaryl, haloaryl, haloalkylaryl, and combinations thereof;
or a pharmaceutically-acceptable salt thereof.

2. The compound of claim 1 wherein $R^2$ is selected from $C_1$–$C_4$ alkyl and trifluoromethyl.

3. The compound of claim 2 wherein Ar is selected from the group consisting of 2-naphthyl, 4-biphenyl, 9-anthryl, 2-fluorenyl, 4-azidophenyl, 4-azidomethylphenyl, 4-(2-azidoethyl)phenyl, 4-(3-azidopropyl)phenyl, 4-(4-azidobutyl)phenyl, 4-(4-azidophenyl)phenyl, 4-(4-azidomethylphenyl)phenyl, 4-methylphenyl, 4-ethylphenyl, 4-propylphenyl, 4-butylphenyl, 4-(2-bromoethyl)phenyl, 4-(3-bromopropyl)phenyl, 4-(4-bromobutyl)phenyl, 4-(trifluoromethyl)phenyl, 4-(4-methylphenyl)phenyl, 4-(4-bromomethylphenyl)phenyl, 4-(4-butylphenyl)phenyl, 4-(4-tert-butylphenyl)phenyl, 2-chlorophenyl, 4-chlorophenyl, 2,4-dichlorophenyl, 3,4-dichlorophenyl, 2,5-dichlorophenyl, 2,4-dimethylphenyl, 2,5-dimethylphenyl, 3,4-dimethylphenyl, 3,5-dimethylphenyl, 4-(4-chlorophenyl)phenyl, 4-(3,5-dichlorophenyl)phenyl, 4-(2,3-dichlorophenyl)phenyl, 4-(3,5-dimethylphenyl)phenyl, 4-(2,4,5-trichlorophenyl)phenyl, 4-(4-trifluoromethylphenyl)phenyl, 2-phenanthrenyl, 3-indolyl, 2-pyrrolyl, and 4-(benzyl)phenyl;

or a pharmaceutically-acceptable salt thereof.

4. A compound of formula II:

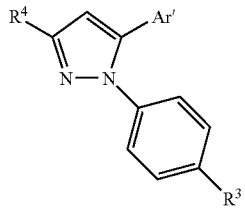

II wherein $R^3$ is selected from the group consisting of carboxyamide and sulfonamide;

$R^4$ is selected from alkyl and haloalkyl; and

Ar' is selected from the group consisting of 4-azidophenyl, 4-(2-azidoethyl)phenyl, 4-(3-azidopropyl)phenyl, 4-(4-azidobutyl)phenyl, 4-(4-azidophenyl)phenyl, 4-(4-azidomethylphenyl)phenyl, 2,5-dimethylphenyl, 4-propylphenyl, 4-bromomethylphenyl, 4-(2-bromoethyl)phenyl, 4-(3-bromopropyl)phenyl, 4-(4-bromobutyl)phenyl, 4-(4-bromomethylphenyl)phenyl, 4-(4-tert-butylphenyl)phenyl, 9-anthryl, 4-(4-butylphenyl)phenyl, 4-(4-methylphenyl)phenyl, 4-(4-chlorophenyl)phenyl, 4-(3,5-dichlorophenyl)phenyl, 4-(2,3-dichlorophenyl)phenyl, 4-(3,5-dimethylphenyl)phenyl, 4-(2,4,5-trichlorophenyl)phenyl, 4-(4-trifluoromethylphenyl)phenyl, 2-phenanthrenyl, 3-indolyl, 2-pyrrolyl, 4-(benzyl)phenyl, and 2-fluorenyl;

or a pharmaceutically-acceptable salt thereof.

5. The compound of claim 4, and the pharmaceutically acceptable salts thereof, selected from the group consisting of 4-[5-(4-azidophenyl)-3-(trifluoromethyl)-1H-pyrazol-1-yl]benzenesulfonamide;

4-[5-(4-(2-azidoethyl)phenyl)-3-(trifluoromethyl)-1H-pyrazol-1-yl]benzenesulfonamide;

4-[5-(4-(3-azidopropyl)phenyl)-3-(trifluoromethyl)-1H-pyrazol-1-yl]benzenesulfonamide;

4-[5-(4-(4-azidobutyl)phenyl)-3-(trifluoromethyl)-1H-pyrazol-1-yl]benzenesulfonamide;

4-[5-(4-(4-butylphenyl)phenyl)-3-(trifluoromethyl)-1H-pyrazol-1-yl]benzenesulfonamide;

4-[5-(4-(4-methylphenyl)phenyl)-3-(trifluoromethyl)-1H-pyrazol-1-yl]benzenesulfonamide;

4-[5-(4-(4-azidophenyl)phenyl)-3-(trifluoromethyl)-1H-pyrazol-1-yl]benzenesulfonamide;

4-[5-(4-(4-azidomethylphenyl)phenyl)-3-(trifluoromethyl)-1H-pyrazol-1-yl]benzenesulfonamide;

4-[5-(4-(4-chlorophenyl)phenyl)-3-(trifluoromethyl)-1H-pyrazol-1-yl]benzenesulfonamide;

4-[5-(4-(3,5-dichlorophenyl)phenyl)-3-(trifluoromethyl)-1H-pyrazol-1-yl]benzenesulfonamide;

4-[5-(4-(2,3-dichlorophenyl)phenyl)-3-(trifluoromethyl)-1H-pyrazol-1-yl]benzenesulfonamide;

4-[5-(4-(3,5-dimethylphenyl)phenyl)-3-(trifluoromethyl)-1H-pyrazol-1-yl]benzenesulfonamide;

4-[5-(4-(2,4,5-trichlorophenyl)phenyl)-3-(trifluoromethyl)-1H-pyrazol-1-yl]benzenesulfonamide;

4-[5-(4-(4-trifluoromethylphenyl)phenyl)-3-(trifluoromethyl)-1H-pyrazol-1-yl]benzenesulfonamide;

4-[5-(2-phenanthrenyl)-3-(trifluoromethyl)-1H-pyrazol-1-yl]benzenesulfonamide;

4-[5-(3-indolyl)-3-(trifluoromethyl)-1H-pyrazol-1-yl]benzenesulfonamide;

4-[5-(2-pyrrolyl)-3-(trifluoromethyl)-1H-pyrazol-1-yl]benzenesulfonamide;

4-[5-(4-benzylphenyl)-3-(trifluoromethyl)-1H-pyrazol-1-yl]benzenesulfonamide;

4-[5-(4-azidophenyl)-3-(trifluoromethyl)-1H-pyrazol-1-yl]benzenecarboxyamide;

4-[5-(4-(2-azidoethyl)phenyl)-3-(trifluoromethyl)-1H-pyrazol-1-yl]benzenecarboxyamide;

4-[5-(4-(3-azidopropyl)phenyl)-3-(trifluoromethyl)-1H-pyrazol-1-yl]benzenecarboxyamide;

4-[5-(4-(4-azidobutyl)phenyl)-3-(trifluoromethyl)-1H-pyrazol-1-yl]benzenecarboxyamide;

4-[5-(4-(4-azidophenyl)phenyl)-3-(trifluoromethyl)-1H-pyrazol-1-yl]benzenecarboxyamide;

4-[5-(4-(4-azidomethylphenyl)phenyl)-3-(trifluoromethyl)-1H-pyrazol-1-yl]benzenecarboxyamide;

4-[5-(2,5-dimethylphenyl)-3-(trifluoromethyl)-1H-pyrazol-1-yl]benzenecarboxyamide;

4-[5-(4-propylphenyl)-3-(trifluoromethyl)-1H-pyrazol-1-yl]benzenecarboxyamide;

4-[5-(4-(2-bromoethyl)phenyl)-3-(trifluoromethyl)-1H-pyrazol-1-yl]benzenecarboxyamide;

4-[5-(4-(4-butylphenyl)phenyl)-3-(trifluoromethyl)-1H-pyrazol-1-yl]benzenecarboxyamide;

4-[5-(4-(4-methylphenyl)phenyl)-3-(trifluoromethyl)-1H-pyrazol-1-yl]benzenecarboxyamide;

4-[5-(4-(3-bromopropyl)phenyl)-3-(trifluoromethyl)-1H-pyrazol-1-yl]benzenecarboxyamide;

4-[5-(4-(4-bromobutyl)phenyl)-3-(trifluoromethyl)-1H-pyrazol-1-yl]benzenecarboxyamide;

4-[5-(4-(4-bromomethylphenyl)phenyl)-3-(trifluoromethyl)-1H-pyrazol-1-yl]benzenecarboxyamide;

4-[5-(4-(4-tert-butylphenyl)phenyl)-3-(trifluoromethyl)-1H-pyrazol-1-yl]benzenecarboxyamide;

4-[5-(9-anthryl)-3-(trifluoromethyl)-1H-pyrazol-1-yl]benzenecarboxyamide;

4-[5-(2-fluorenyl)-3-(trifluoromethyl)-1H-pyrazol-1-yl]benzenecarboxyamide;

4-[5-(4-(4-chlorophenyl)phenyl)-3-(trifluoromethyl)-1H-pyrazol-1-yl]benzenecarboxyamide;

4-[5-(4-(3,5-dichlorophenyl)phenyl)-3-(trifluoromethyl)-1H-pyrazol-1-yl]benzenecarboxyamide;

4-[5-(4-(2,3-dichlorophenyl)phenyl)-3-(trifluoromethyl)-1H-pyrazol-1-yl]benzenecarboxyamide;

4-[5-(4-(3,5-dimethylphenyl)phenyl)-3-(trifluoromethyl)-1H-pyrazol-1-yl]benzenecarboxyamide;

4-[5-(4-(2,4,5-trichlorophenyl)phenyl)-3-(trifluoromethyl)-1H-pyrazol-1-yl]benzenecarboxyamide;

4-[5-(4-(4-trifluoromethylphenyl)phenyl)-3-(trifluoromethyl)-1H-pyrazol-1-yl]benzenecarboxyamide;

4-[5-(2-phenanthrenyl)-3-(trifluoromethyl)-1H-pyrazol-1-yl]benzenecarboxyamide;

4-[5-(3-indolyl)-3-(trifluoromethyl)-1H-pyrazol-1-yl]benzenecarboxyamide;

4-[5-(2-pyrrolyl)-3-(trifluoromethyl)-1H-pyrazol-1-yl]benzenecarboxyamide; and

4-[5-(4-benzylphenyl)-3-(trifluoromethyl)-1H-pyrazol-1-yl]benzenecarboxyamide.

6. The compound of claim 5 wherein the compound is 4-[5-(2-phenanthrenyl)-3-(trifluoromethyl)-1H-pyrazol-1-yl]benzenesulfonamide.

* * * * *